US010202660B2

(12) United States Patent
Balan et al.

(10) Patent No.: US 10,202,660 B2
(45) Date of Patent: Feb. 12, 2019

(54) METHODS FOR INCREASING SUGAR YIELD WITH SIZE-ADJUSTED LIGNOCELLULOSIC BIOMASS PARTICLES

(71) Applicant: BOARD OF TRUSTEES OF MICHIGAN STATE UNIVERSITY, East Lansing, MI (US)

(72) Inventors: Venkatesh Balan, East Lansing, MI (US); Bruce E. Dale, Mason, MI (US); Shuhaida Harun, Senawang (MY)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 896 days.

(21) Appl. No.: 14/382,370

(22) PCT Filed: Mar. 1, 2013

(86) PCT No.: PCT/US2013/028689
§ 371 (c)(1),
(2) Date: Sep. 2, 2014

(87) PCT Pub. No.: WO2013/131015
PCT Pub. Date: Sep. 6, 2013

(65) Prior Publication Data
US 2015/0125907 A1 May 7, 2015

Related U.S. Application Data

(60) Provisional application No. 61/606,139, filed on Mar. 2, 2012.

(51) Int. Cl.
| | | |
|---|---|---|
| *C13K 1/02* | (2006.01) |
| *C12P 7/10* | (2006.01) |
| *C12P 7/16* | (2006.01) |
| *C08H 8/00* | (2010.01) |
| *C12P 19/14* | (2006.01) |
| *C07C 31/08* | (2006.01) |
| *C07C 31/10* | (2006.01) |
| *C12M 1/40* | (2006.01) |
| *C12M 1/33* | (2006.01) |
| *C12P 19/02* | (2006.01) |
| *C13K 13/00* | (2006.01) |
| *A23K 10/32* | (2016.01) |
| *A23K 10/30* | (2016.01) |
| *A23K 10/37* | (2016.01) |
| *A23K 20/111* | (2016.01) |

(52) U.S. Cl.
CPC .............. *C13K 1/02* (2013.01); *A23K 10/30* (2016.05); *A23K 10/32* (2016.05); *A23K 10/37* (2016.05); *A23K 20/111* (2016.05); *C07C 31/08* (2013.01); *C07C 31/10* (2013.01); *C08H 8/00* (2013.01); *C12M 21/18* (2013.01); *C12M 45/02* (2013.01); *C12P 7/10* (2013.01); *C12P 7/16* (2013.01); *C12P 19/02* (2013.01); *C12P 19/14* (2013.01); *C13K 13/002* (2013.01); *C12P 2201/00* (2013.01); *Y02E 50/10* (2013.01); *Y02E 50/16* (2013.01); *Y02P 60/877* (2015.11)

(58) Field of Classification Search
CPC ...................................................... A23K 10/30
See application file for complete search history.

(56) References Cited

U.S. PATENT DOCUMENTS

| | | | |
|---|---|---|---|
| 3,259,501 A | 7/1966 | Ulrey | |
| 3,707,436 A | 12/1972 | O'Connor | |
| 4,064,276 A | 12/1977 | Conradsen et al. | |
| 4,263,744 A | 4/1981 | Stoller | |
| 4,356,196 A | 10/1982 | Hultquist | |
| 4,370,351 A | 1/1983 | Harper | |
| 4,461,648 A | 7/1984 | Foody | |
| 4,526,791 A | 7/1985 | Young | |
| 4,589,334 A | 5/1986 | Andersen | |
| 4,600,590 A | 7/1986 | Dale | |
| 4,624,805 A | 11/1986 | Lawhon | |
| 4,642,287 A | 2/1987 | Inoi et al. | |
| 4,644,060 A | 2/1987 | Chou | |
| 4,848,026 A | 7/1989 | Dunn-Coleman et al. | |
| 5,037,663 A | 8/1991 | Dale | |
| 5,047,332 A | 9/1991 | Chahal | |
| 5,171,592 A | 12/1992 | Holtzapple et al. | |
| 5,370,999 A | 12/1994 | Stuart | |
| 5,473,061 A | 12/1995 | Bredereck et al. | |
| 5,736,032 A | 4/1998 | Cox et al. | |
| 5,865,898 A | 2/1999 | Holtzapple et al. | |
| 5,939,544 A | 8/1999 | Karstens et al. | |
| 6,106,888 A * | 8/2000 | Dale ................... | B29C 47/0004 426/516 |
| 6,176,176 B1 | 1/2001 | Dale et al. | |
| 6,255,505 B1 | 7/2001 | Bijl et al. | |
| 6,416,621 B1 | 7/2002 | Karstens | |
| 6,444,437 B1 | 9/2002 | Sporleder et al. | |

(Continued)

FOREIGN PATENT DOCUMENTS

| | | |
|---|---|---|
| AU | 756976 B2 | 1/2003 |
| CA | 2368872 A1 | 10/2000 |

(Continued)

OTHER PUBLICATIONS

Search Report & Written Opinion received for Singapore Patent Application No. 11201406820T, dated Dec. 18, 2015, 10 pages.

(Continued)

Primary Examiner — Thomas J. Visone
(74) Attorney, Agent, or Firm — Clark IP Law, PLC

(57) ABSTRACT

A method of increasing sugar yield in a bioproduct production process is provided comprising pretreating one or more size-adjusted lignocellulosic biomass (LCB) particles with a pretreatment, such as an ammonia pretreatment, wherein the one or more size-adjusted LCB particles form a substrate, with the one or more particles having an average particle size in at least one dimension greater than 5 mm.

17 Claims, 16 Drawing Sheets

(56) References Cited

U.S. PATENT DOCUMENTS

| | | |
|---|---|---|
| 6,620,292 B2 | 9/2003 | Wingerson |
| 7,049,485 B2 | 5/2006 | Sticklen et al. |
| 7,187,176 B2 | 3/2007 | Lim et al. |
| 7,371,926 B2 | 5/2008 | Sticklen et al. |
| 7,371,962 B2 | 5/2008 | Zuppero et al. |
| 7,494,675 B2 | 2/2009 | Abbas et al. |
| 7,537,744 B2 | 5/2009 | Benderly et al. |
| 7,585,652 B2 | 9/2009 | Foody et al. |
| 7,771,565 B2 | 8/2010 | Kirov et al. |
| 7,910,338 B2 | 3/2011 | Hennessey et al. |
| 7,915,017 B2 | 3/2011 | Dale |
| 7,937,851 B2 | 5/2011 | Rajagopalan et al. |
| 8,020,342 B2 | 9/2011 | Karpik |
| 8,030,030 B2 | 10/2011 | Varanasi et al. |
| 8,193,324 B2 | 6/2012 | Hallberg et al. |
| 8,367,378 B2 | 2/2013 | Balan et al. |
| 8,394,611 B2 | 3/2013 | Dale et al. |
| 8,419,900 B2 | 4/2013 | Baba et al. |
| 8,444,925 B2 | 5/2013 | Baba |
| 8,551,549 B2 | 10/2013 | Zeeck |
| 8,651,403 B2 | 2/2014 | Camp et al. |
| 8,673,031 B2 | 3/2014 | Dale et al. |
| 8,771,425 B2 | 7/2014 | Dale |
| 8,846,123 B2 | 9/2014 | Zeeck |
| 8,945,245 B2 | 2/2015 | Bals et al. |
| 8,968,515 B2 | 3/2015 | Balan et al. |
| 8,980,599 B2 | 3/2015 | Tolan et al. |
| 9,644,222 B2 | 5/2017 | Balan et al. |
| 2003/0044951 A1 | 3/2003 | Sporleder et al. |
| 2005/0233423 A1 | 10/2005 | Berka et al. |
| 2006/0014260 A1 | 1/2006 | Fan et al. |
| 2006/0130396 A1 | 6/2006 | Werner |
| 2006/0177917 A1 | 8/2006 | Warzywoda et al. |
| 2007/0029252 A1 | 2/2007 | Dunson, Jr. et al. |
| 2007/0031918 A1 | 2/2007 | Dunson, Jr. et al. |
| 2007/0037259 A1 | 2/2007 | Hennessey et al. |
| 2007/0192900 A1 | 8/2007 | Sticklen |
| 2007/0202214 A1 | 8/2007 | Lewis et al. |
| 2007/0227063 A1 | 10/2007 | Dale et al. |
| 2007/0287795 A1 | 12/2007 | Huda et al. |
| 2008/0008783 A1 | 1/2008 | Dale |
| 2008/0057555 A1 | 3/2008 | Nguyen |
| 2008/0171297 A1 | 7/2008 | Reynolds et al. |
| 2008/0229657 A1 | 9/2008 | Senyk et al. |
| 2008/0256851 A1 | 10/2008 | Lumb |
| 2008/0280236 A1 | 11/2008 | Wright |
| 2009/0011474 A1* | 1/2009 | Balan .................... C12P 7/06 435/99 |
| 2009/0042259 A1 | 2/2009 | Dale et al. |
| 2009/0053770 A1 | 2/2009 | Hennessey et al. |
| 2009/0053771 A1 | 2/2009 | Dale et al. |
| 2009/0061486 A1 | 3/2009 | Edwards et al. |
| 2009/0093027 A1 | 4/2009 | Balan et al. |
| 2009/0178671 A1 | 7/2009 | Ahring et al. |
| 2009/0221042 A1 | 9/2009 | Dale et al. |
| 2009/0318670 A1 | 12/2009 | Dale et al. |
| 2010/0159521 A1 | 6/2010 | Cirakovic et al. |
| 2010/0267999 A1 | 10/2010 | Lau et al. |
| 2010/0279361 A1 | 11/2010 | South et al. |
| 2010/0291650 A1* | 11/2010 | Larsen ................ D21C 5/005 435/165 |
| 2011/0192559 A1 | 8/2011 | Venkatesh et al. |
| 2011/0201091 A1 | 8/2011 | Dale |
| 2011/0290114 A1 | 12/2011 | Campbell et al. |
| 2011/0300269 A1 | 12/2011 | Dale et al. |
| 2012/0064574 A1 | 3/2012 | Tokuyasu et al. |
| 2012/0071308 A1 | 3/2012 | Sekar |
| 2012/0085505 A1 | 4/2012 | Sabourin |
| 2012/0125548 A1 | 5/2012 | Cohen |
| 2012/0125551 A1 | 5/2012 | Cohen et al. |
| 2012/0187228 A1 | 7/2012 | Camp et al. |
| 2012/0325202 A1 | 12/2012 | Dale |
| 2013/0196398 A1 | 8/2013 | Bals et al. |
| 2013/0217073 A1 | 8/2013 | Chundawat et al. |
| 2013/0280762 A1 | 10/2013 | Dale et al. |
| 2013/0289268 A1 | 10/2013 | Teymouri et al. |
| 2014/0038243 A1* | 2/2014 | Balan .................... C12P 7/10 435/99 |
| 2014/0227757 A1 | 8/2014 | Jin et al. |

FOREIGN PATENT DOCUMENTS

| | | |
|---|---|---|
| CA | 2573046 A1 | 1/2006 |
| CA | 2610797 A1 | 12/2006 |
| CA | 2752604 A1 | 8/2010 |
| CA | 2797193 A1 | 10/2011 |
| CA | 2762985 C | 7/2013 |
| CA | 2650860 C | 9/2013 |
| CA | 2737704 C | 11/2013 |
| CA | 2760840 C | 12/2015 |
| CN | 101223273 A | 7/2008 |
| CN | 102597247 A | 7/2012 |
| CN | 102939388 A | 2/2013 |
| DE | 20301645 U1 | 4/2003 |
| EP | 0144930 A2 | 6/1985 |
| EP | 1247781 A2 | 10/2002 |
| EP | 1533279 A1 | 5/2005 |
| EP | 1690944 A1 | 8/2006 |
| EP | 2411492 A2 | 2/2012 |
| EP | 2561084 A2 | 2/2013 |
| EP | 2841588 A2 | 3/2015 |
| GB | 1310835 A | 3/1973 |
| GB | 1381728 A | 1/1975 |
| GB | 2122864 A | 1/1984 |
| IN | 249187 A1 | 10/2011 |
| JP | 2008-161125 A | 7/2008 |
| JP | 2008-535664 | 9/2008 |
| JP | 2011-160753 A | 8/2011 |
| RU | 2215755 C1 | 11/2003 |
| WO | 85/00133 A1 | 1/1985 |
| WO | 2000/061858 A1 | 10/2000 |
| WO | 2001/032715 A1 | 5/2001 |
| WO | 2002/037981 A2 | 5/2002 |
| WO | 2004/033920 A1 | 4/2004 |
| WO | 2006/128304 A1 | 12/2006 |
| WO | 2007/005918 A2 | 1/2007 |
| WO | 2007/005918 A3 | 8/2007 |
| WO | 2007/130337 A1 | 11/2007 |
| WO | 2008/020901 A2 | 2/2008 |
| WO | 2008/114139 A2 | 9/2008 |
| WO | 2008/114139 A3 | 12/2008 |
| WO | 2009/011474 A1 | 1/2009 |
| WO | 2009025547 A1 | 2/2009 |
| WO | 2009/045527 A1 | 4/2009 |
| WO | 2010/098408 A1 | 9/2010 |
| WO | 2010/121348 A1 | 10/2010 |
| WO | 2010/135679 A1 | 11/2010 |
| WO | 2010/147218 A1 | 12/2010 |
| WO | 2011/028543 A2 | 3/2011 |
| WO | 2011028543 A2 | 3/2011 |
| WO | 2011/046818 A2 | 4/2011 |
| WO | 2011/080154 A1 | 7/2011 |
| WO | 2011/125056 A1 | 10/2011 |
| WO | 2011/133571 A2 | 10/2011 |
| WO | 2011157427 A1 | 12/2011 |
| WO | 2011/133571 A3 | 1/2012 |
| WO | 2012/012594 A1 | 1/2012 |
| WO | 2012051523 A1 | 4/2012 |
| WO | 2012/071312 A2 | 5/2012 |
| WO | 2012/088429 A2 | 6/2012 |
| WO | 2013/106113 A2 | 7/2013 |
| WO | 2013/131015 A1 | 9/2013 |
| WO | 2013/106113 A3 | 10/2013 |
| WO | 2013/163571 A2 | 10/2013 |
| WO | 2013/163571 A3 | 3/2014 |

OTHER PUBLICATIONS

Final Office Action received for U.S. Appl. No. 13/997,043, dated Apr. 18, 2016, 22 pages.

Final Office Action received for U.S. Appl. No. 14/251,921, dated Apr. 11, 2016, 17 pages.

(56) References Cited

OTHER PUBLICATIONS

Preliminary Rejection Received for Brazilian Patent Application No. PI0711139-8, dated Jan. 22, 2016, (English Translation only), 6 pages.
Preliminary Rejection received for Brazilian Patent Application No. PI0722418-4, dated Feb. 5, 2016, (English Translation only), 4 pages.
Office Action received for Canadian Patent Application No. 2,870,758, dated Mar. 9, 2016, 5 pages.
Office Action received for Chinese Patent Application No. 201380022053.7, dated Jan. 8, 2016 (7 pages of English Translation and 6 pages of Official Copy).
Tumuluru et al., Idaho National Laboratory, A Review on Biomass Densification Technologies for Energy Application, http://www.inl.com, Aug. 2010, 96 pages.
Wen et al., Isolation and characterization of hemicellulose and cellulose from sugar beet pulp, Journal of Food Science, vol. 53, No. 3, 1988, pp. 826-829, 4 pages.
Lau et al., "Cellulosic Ethanol Production from AFEX-treated Corn Stover Using *Saccharomyces cerevisiae* 424A (LNH-ST)", PNAS, vol. 106, No. 5, Feb. 3, 2009, pp. 1368-1373.
Lau et al., "Comparing the Fermentation Performance of *Escherichia coli* KO11, *Saccharomyces cerevisiae* 424A (LNH-ST) and Zymomonas mobilis AX101 for Cellulosic Ethanol Production", Biotechnology for Biofuels, vol. 3, No. 11, 2010, 10 pages.
Lau et al., "Ethanol Fermentation of *E. coli* KO11 in Hydrolysate from AFEX-treated Corn Stover", Biomass Conversion Research Laboratory, Department of Chemical Engineering and Materials Science, Michigan State University, Apr. 30, 2006., 1 page.
Lau et al., "The Impacts of Pretreatment on the Fermentability of Pretreated Lignocellulosic Biomass: A Comparative Evaluation between Ammonia Fiber Expansion and Dilute Acid Pretreatment", Biotechnology for Biofuels, vol. 2, No. 30, 2009, 11 pages.
Laureano-Perez et al., "Understanding Factors That Limit Enzymatic Hydrolysis of Biomass—Characterization of Pretreated Corn Stover", Applied Biochemistry and Biotechnology, vol. 121-124, 2005, pp. 1081-1099.
Lin et al., "Ethanol Fermentation From Biomass Resources: Current State and Prospects", Applied Microbiology and Biotechnology, vol. 69, No. 6, Feb. 2006, pp. 627-642.
Liu et al., "Partial Flow of Compressed-Hot Water through Corn Stover to Enhance Hemicellulose Sugar Recovery and Enzymatic Digestibility of Cellulose", Bioresource Technology, vol. 96, No. 18, 2005, pp. 1978-1985.
Lloyd et al., "Combined Sugar Yields for Dilute Sulfuric Acid Pretreatment of Corn Stover Followed by Enzymatic Hydrolysis of the Remaining Solids", Bioresource Technology, vol. 96, No. 18, Dec. 2005, pp. 1967-1977.
Lovrien et al., "Assays for Total Protein", Current Protocols in Protein Science, Detection and Assay Methods, 3.4.1., Supplement 1, 1995, 24 pages.
Lu et al., "Cellulase Adsorption and an Evaluation of Enzyme Recycle During Hydrolysis of Steam-Exploded Softwood Residues", Applied Biochemistry and Biotechnology, vols. 98-100, 2002, pp. 641-654.
Lynd et al., "Microbial Cellulose Utilization: Fundamentals and Biotechnology", Microbiology and Molecular Biology Reviews, vol. 66, No. 3, Sep. 2002, pp. 506-577.
Madakadze et al., "Cutting Frequency and Nitrogen Fertilization Effects on Yield and Nitrogen Concentration of Switchgrass in a Short Season Area", Crop Science, vol. 39, No. 2, Mar.-Apr. 1999, pp. 552-557.
Mani et al., "Economics of Producing Fuel Pellets from Biomass", Applied Engineering in Agriculture, vol. 22, No. 3, 2006, pp. 421-426.
Mantanis et al., "Swelling of Compressed Cellulose Fiber Webs in Organic Liquids", Cellulose, vol. 2, No. 1, 1995, pp. 1-22.
Marshall et al., "Complete Rations for Dairy Cattle. II. Sugarcane Bagasse Pellets as Roughage in Blended Rations for Lactating Cows", Journal of Dairy Science, vol. 58, No. 6, Jun. 1975, pp. 896-900.
Miller, Norman G., "Phase I Biomass Enhanced Refined Lignite Demonstration Project", Dec. 15, 2008, 24 pages.
Mosier et al., "Features of Promising Technologies for Pretreatment of Lignocellulosic Biomass", Bioresource Technology, vol. 96, 2005, pp. 673-686.
Mosier et al., "Optimization of pH Controlled Liquid Hot Water Pretreatment of Corn Stover", Bioresource Technology, vol. 96, 2005, pp. 1986-1993.
Nwodo et al., "Xylanase Production of Aspergillus niger and Penicillium chrysogenum from Ammonia Pretreated Cellulosic Waste", Research Journal of Microbiology, vol. 3, No. 4, 2008, pp. 246-253.
Ohara, H., "Biorefinery", Applied Microbiology and Biotechnology, vol. 62, No. 5-6, Oct. 2003, pp. 474-477.
Ordonez et al., "Obtaining a Protein Concentrate from Integral Defatted Sunflower Flour", Bioresource Technology, vol. 78, No. 2, 2001, pp. 187-190.
Ozturk et al., "Splitting Tendency of Cellulosic Fibers. Part 2: Effects of Fiber Swelling in Alkali Solutions", Cellulose, vol. 13, No. 4, Aug. 2006, pp. 403-409.
Pandey et al., "Economic Utilization of Crop Residues for Value Addition: A Futuristic Approach", Journal of Scientific & Industrial Research, vol. 59, Jan. 2000, pp. 12-22.
Park et al., "Investigation and Optimization of the Factors Influencing Sorghum Protein Extraction", Journal of Agricultural and Food Chemistry, vol. 51, No. 24, Oct. 2003, pp. 7050-7054.
Paul et al., "Liquid-Vapor Interfacial Properties of Water-Ammonia Mixtures: Dependence on Ammonia Concentration", The Journal of Chemical Physics, vol. 123, No. 17, 2005, 10 pages.
Perry et al., "Reaction Kinetics and Reactor Design", Chemical Engineers' Handbook, Fourth Edition, 1963, 6 pages.
Piva et al., "Detoxification Methods of Aflatoxins. A Review", Nutrition Research, vol. 15, No. 5, May 1995, pp. 767-776.
Prévot-D'Alvise et al., "Development of a Pilot Process for the Production of Alfalfa Peptide Isolate", Journal of Chemical Technology and Biotechnology, vol. 78, No. 5, May 2003, pp. 518-528.
Ragauskas et al., "The Path Forward for Biofuels and Biomaterials", Science, vol. 311, No. 5760, Jan. 27, 2006, pp. 484-489.
Rajagopalan et al., "Enhancing Profitability of Dry Mill Ethanol Plants", Applied Biochemistry and Biotechnology, vol. 120, No. 1, 2005, pp. 37-50.
Rausch et al., "The Future of Coproducts from Corn Processing", Applied Biohemistry and Biotechnology, vol. 128, 2006, pp. 47-86.
Renewable Fuels Association, "From Niche to Nation—Ethanol Industry Outlook 2006", Feb. 2006, 24 pages.
Rijal et al., "Combined Effect of Pelleting and Pretreatment on Enzymatic Hydrolysis of Switchgrass", Bioresource Technology, vol. 116, 2012, pp. 36-41.
Rollin et al., "Increasing Cellulose Accessibility is More Important Than Removing Lignin: A Comparison of Cellulose Solvent-Based Lignocellulose Fractionation and Soaking in Aqueous Ammonia", Biotechnology and Bioengineering, vol. 108, No. 1, Jan. 2011, pp. 22-30.
Roman-Ponce et al., "Complete Rations for Dairy Cattle. V. Interaction of Sugarcane Bagasse Quantity and Form with Soybean Meal,Urea, and Starea", Journal of Dairy Science, vol. 58, No. 9, Sep. 1975, pp. 1320-1327.
Rosa et al., "Integrated Production of Ethanol Fuel and Protein From Coastal Bermudagrass", Applied Biochemistry and Biotechnology, vol. 45/46, No. 1, 1994, pp. 483-497.
Saha, Badal C., "Hemicellulose Bioconversion", Journal of Industrial Microbiology and Biotechnology, vol. 30, No. 5, May 2003, pp. 279-291.
Sanchez et al., "Biodegradation of Viticulture Wastes by Pleurotus: A Source of Microbial and Human Food and Its Potential Use in Animal Feeding", Journal of Agricultural and Food Chemistry, vol. 50, No. 9, Apr. 2002, pp. 2537-2542.
Sanderson et al., "Switchgrass As a Sustainable Bioenergy Crop", Bioresource Technology, vol. 56, No. 1, Apr. 1996, pp. 83-93.

(56) References Cited

OTHER PUBLICATIONS

Sarikaya et al., "Solid-State Fermentation of Lignocellulosic Plant Residues from *Brassica napus* by Pleurotus Ostreatus", Applied Biochemistry and Biotechnology,vol. 82, No. 1, Oct. 1999, pp. 1-15.
Sendich et al., "Recent Process Improvements for the Ammonia Fiber Expansion (AFEX) Process and Resulting Reductions in Minimum Ethanol Selling Price", Bioresource Technology, vol. 99, 2008, pp. 8429-8435.
Singh et al., "Composting of a Crop Residue through Treatment with Microorganisms and Subsequent Vermicomposting", Bioresource Technology,vol. 85, No. 2, Nov. 2002, pp. 107-111.
Singhania et al., "Advancement and Comparative Profiles in the Production Technologies Using Solid-State and Submerged Fermentation for Microbial Cellulases", Enzyme and Microbial Technology, vol. 46, 2010, pp. 541-549.
Sluiter et al., "Determination of Structural Carbohydrates and Lignin in Biomass", National Renewable Energy Laboratory, Laboratory Analytical Procedure (LAP), Apr. 25, 2008, 17 pages.
Sokhansanj et al., "Biomass Densification—Cubing Operations and Costs for Corn Stover", Applied Engineering in Agriculture, vol. 20, No. 4, 2004, pp. 495-499.
Somerville et al., "Toward a Systems Approach to Understanding Plant Cell Walls", Science, vol. 306, No. 5705, Dec. 24, 2004, pp. 2206-2211.
Steele et al., "Enzyme Recovery and Recycling Following Hydrolysis of Ammonia Fiber Explosion—Treated Corn Stover", Applied Biochemistry and Biotechnology, vol. 121-124, No. 1-3, 2005, pp. 901-910.
Sukumaran et al., "Cellulase Production Using Biomass Feed Stock and Its Application in Lignocellulose Saccharification for Bio-Ethanol Production", Renewable Energy, vol. 34, No. 2, Feb. 2009, pp. 421-424.
Sulbaran-De-Ferrer et al., "Enzymatic Hydrolysis of Ammonia-Treated Rice Straw", Applied Biochemistry and Biotechnology, vol. 105-108, 2003, pp. 155-164.
Non Final Office Action received for U.S. Appl. No. 13/997,043, dated Jul. 17, 2015, 16 pages.
Non Final Office Action received for U.S. Appl. No. 13/886,021, dated Oct. 30, 2015, 22 pages.
Non Final Office Action received for U.S. Appl. No. 14/251,921, dated Nov. 16, 2015, 12 pages.
Final Office Action received for U.S. Appl. No. 13/642,052, dated Jun. 18, 2015, 32 pages.
Restriction Requirement received for U.S. Appl. No. 14/251,921 dated Sep. 3, 2015, 6 pages.
Office Action received for Canadian Patent Application No. 2,870,758, dated Jul. 24, 2015, 6 pages.
Extended European Search Report Received for European Patent Application No. 14174649.5, dated Dec. 23, 2014, 8 pages.
Communication Pursuant to Article 94(3) EPC received for European Patent Application No. 14174649.5, dated Sep. 30, 2015, 5 pages.
Preliminary Rejection received for Brazilian Patent Application No. PI0711139-8, dated Sep. 29, 2015, 11 pages.
Preliminary Rejection received for Brazilian Patent Application No. PI0722418-4, dated Sep. 29, 2015, 6 pages.
Office Action received for Mexican Patent Application No. MX/a/2014/012737 dated Dec. 23, 2014, 7 pages.
Office Action received for Vietnamese Patent Application No. 1-2014-03985, dated Feb. 13, 2015, 2 pages.
Kim et al., "Biofuels, Methods and Protocols", Methods in Molecular Biology, vol. 581, ISSN: 1064-3745, Chapter 6, Aug. 2009, pp. 79-91.
Iyer, et al., "Ammonia Recycled Percolation Process for Pretreatment of Herbaceous Biomass", Applied Biochemistry and Biotechnology, vol. 57/58, 1996, pp. 121-132.
Non-Final Office Action received for U.S. Appl. No. 14/251,921, dated Nov. 2, 2016, 12 pages.
Office Action received for Canadian Patent Application No. 2,870,758, dated Aug. 10, 2016, 5 pages.
Office Action Received for Chinese Application No. 201380022053.7, dated Nov. 16, 2016 (2 pages of English Translation and 5 pages of Official Copy).
Office Action Received for Japanese Patent Application No. 2015-509190, dated Feb. 14, 2017, 4 pages.
Balan et al., Enzymatic Digestibility and Pretreatment Degradation Products of AFEX-Treated Hardwoods (*Populus nigra*), Biotechnol. Prog., Mar. 26, 2009, pp. 365-375, vol. 25, No. 2.
Shao et al., Enzymatic digestibility and ethanol fermentability of AFEX-treated starch-rich lignocellulosics such as corn silage and whole corn plant, Biotechnology for Biofuels, Jun. 9, 2010, pp. 1-10, vol. 3, No. 12.
Sun et al., "Hydrolysis of Lignocellulosic Materials for Ethanol Production: A Review", Bioresource Technology, vol. 83, No. 1, 2002, pp. 1-11.
Sunopta Bioprocess Group, "A Leader in the Processing of Value Added Compounds from Plant Biomass Materials", Customer Manual, 2007, 20 pages.
Suto et al., "Induction and Catabolite Repression Mechanisms of Cellulase in Fungi", Journal of Bioscience and Bioengineering, vol. 92, No. 4, 2001, pp. 305-311.
Tabil et al., "Biomass Feedstock Pre-Processing—Part 1: Pre-Treatment", Chapter 18, Biofuel's Engineering Process Technology, Aug. 2011, pp. 411-438.
Taniguchi et al., "Evaluation of Pretreatment with Pleurotus Ostreatus for Enzymatic Hydrolysis of Rice Straw", Journal of Bioscience and Bioengineering, vol. 100, No. 6, Dec. 2005, pp. 637-643.
Tanner Industries, Inc., "Anhydrous Ammonia", Customer Manual, Dec. 2006, 17 pages.
Teymouri et al., "Hydrolysis of Ground and Unground AFEX Treated Corn Stover with Different Combinations of Cellulase and Xylanase", 27th Symposium on Biotechnology for Fuels and Chemicals, May 1-4, 2005, 21 pages.
Teymouri et al., "Optimization of the Ammonia Fiber Explosion (AFEX) Treatment Parameters for Enzymatic Hydrolysis of Corn Stover", Bioresource Technology, vol. 96, 2005, pp. 2014-2018.
Theerarattananoon et al., "Effects of the Pelleting Conditions on Chemical Composition and Sugar Yield of Corn Stover, Big Bluestem, Wheat Straw, and Sorghum Stalk Pellets", Bioprocess Biosyst. Eng., vol. 35, No. 4, May 2012, pp. 615-623.
Tolan, Jeffrey S., "Fuel-oriented Biorefineries—logen's Demonstration Process for Producing Ethanol from Cellulosic Biomass", Biorefineries—Industrial Processes and Products, Chapter 9, 2006, pp. 193-208.
Turner et al., "Disruption of Forage Structure with an Ammonia Fiber Explosion Process", Proceedings Western Section, American Society of Animal Science, vol. 41, 1990, pp. 494-497.
Uraki et al., "Body Temperature-Responsive Gels Derived from Hydroxypropylcellulose Bearing Lignin II: Adsorption and Release Behavior", Cellulose, vol. 13, No. 3, Jun. 2006, pp. 225-234.
Urribarri et al., "Leaf Protein from Ammonia-Treated Dwarf Elephant Grass (*Pennisetum purpureum* Schum cv. Mott)", Applied Biochemistry and Biotechnology, vol. 121-124, 2005, pp. 721-730.
Van Horn et al., "Complete Rations for Growing Dairy Replacements Utilizing By-Product Feedstuffs", Journal of Dairy Science, vol. 63, 1980, pp. 1465-1474.
Vrije et al., "Pretreatment of Miscanthus for Hydrogen Production by Thermotoga Elfii", International Journal of Hydrogen Energy, vol. 27, 2002, pp. 1381-1390.
Waiss et al., "Improving Digestibility of Straws for Ruminant Feed by Aqueous Ammonia", Journal of Animal Science, vol. 35, No. 1, 1972, pp. 109-112.
Walter, A., "Industrial Uses of Biomass Energy—New Technologies for Modern Biomass Energy Carriers", Taylor and Francis, Chapter 9, edited by Rosillo-Calle F., Bajay SV, Rothman H, 2000, pp. 200-253.
Wang et al., "Cost Estimates and Sensitivity Analyses for the Ammonia Fiber Explosion Process", Applied Biochemistry and Biotechnology, vol. 70-72, No. 1, 1998, pp. 51-66.
Warzywoda et al., "Production and Characterization of Cellulolytic Enzymes from Trichoderma reesei Grown on Various Carbon Sources", Bioresource Technology, vol. 39, 1992, pp. 125-130.

(56) References Cited

OTHER PUBLICATIONS

Wheals et al., "Fuel Ethanol after 25 Years", Trends in Biotechnology, Department of Biology and Biochemistry, vol. 17, No. 12, Dec. 1999, pp. 482-487.
Williams et al., "An Initial Assessment of Spent Mushroom Compost as a Potential Energy Feedstock", Bioresource Technology, vol. 79, Sep. 2001, pp. 227-230.
Wilson, Jonathan, "A Cost Analysis for the Densification and Transportation of Cellulosic Biomass for Ethanol Production", A Thesis, 2011, 86 pages.
Wyman et al., "Comparative Sugar Recovery Data From Laboratory Scale Application of Leading Pretreatment Technologies to Corn Stover", Bioresource Technology, vol. 96, No. 18, 2005, pp. 2026-2032.
Wyman et al., "Coordinated Development of Leading Biomass Pretreatment Technologies", Bioresource Technology, vol. 96, No. 18, 2005, pp. 1959-1966.
Ye et al., "Improving Accessibility and Reactivity of Cellulose of Annual Plants for the Synthesis of Methylcellulose", Cellulose, vol. 12, No. 5, Oct. 2005, pp. 507-515.
Zhang et al., "A Transition from Cellulose Swelling to Cellulose Dissolution by o-Phosphoric Acid: Evidence from Enzymatic Hydrolysis and Supramolecular Structure", Biomacromolecules, vol. 7, No. 2, Feb. 2006, pp. 644-648.
Zhang et al., "Oyster Mushroom Cultivation with Rice and Wheat Straw", Bioresource Technology, vol. 82, No. 3, May 2002, pp. 277-284.
Zhang et al., "The Effect of Different Treatment Conditions on Biomass Binder Preparation for Lignite Briquette", Fuel Processing Technology, vol. 73, 2001, pp. 185-196.
Zhang et al., "Toward an Aggregated Understanding of Enzymatic Hydrolysis of Cellulose: Noncomplexed Cellulase Systems", Biotechnology and Bioengineering, vol. 88, No. 7, Dec. 30, 2004, pp. 797-824.
Zhong et al., "Optimization of Enzymatic Hydrolysis and Ethanol Fermentation from AFEX-Treated Rice Straw", Applied Microbiology and Biotechnology, vol. 84, No. 4, Springer-Verlag, Sep. 2009, pp. 667-676.
Zhou et al., "Gene Integration and Expression and Extracellular Secretion of Erwinia chrysanthemi Endoglucanase CelY (celY) and CelZ (celZ) in Ethanologenic Klebsiella oxytoca P2†", Applied and Environmental Microbiology, vol. 67, No. 1, 2001, pp. 6-14.
Zhu et al., "Cocurrent Downflow Circulating Fluidized Bed (Downer) Reactors—A State of the Art Review", The Canadian Journal of Chemical Engineering, vol. 73, Oct. 1995, pp. 662-677.
"Topic 3 R&D on Processes for Solid, Liquid and Gaseous Fuels From Biomass", 20th European Biomass Conference and Exhibition, 2012, 26 pages.
Extended European Search Report received for European Patent Application No. 07776479.3, dated May 26, 2010, 6 pages.
Official Communication pursuant to Article 94(3) EPC received for European Patent Application No. 07776479.3, dated May 30, 2012, 6 pages.
Official Communication pursuant to Article 94(3) EPC received for European Patent Application No. 07776479.3, dated Dec. 5, 2012, 4 pages.
Official Communication pursuant to Rules 161(2) and 162 EPC received for European Patent Application No. 10778488.6, dated Dec. 30, 2011, 2 pages.
Official Communication pursuant to Article 94(3) EPC received for European Patent Application No. 10814256.3, dated Sep. 6, 2013, 4 pages.
Non-Final Office Action received for U.S. Appl. No. 11/719,158, dated Apr. 1, 2009, 6 pages.
Final Office Action received for U.S. Appl. No. 11/719,158, dated Aug. 4, 2010, 7 pages.
Notice of Allowance received for U.S. Appl. No. 11/719,158, dated Jan. 6, 2011, 4 pages.
Non Final Office Action received for U.S. Appl. No. 11/729,632, dated May 6, 2009, 5 pages.
Notice of Allowance received for U.S. Appl. No. 11/729,632, dated Nov. 16, 2009, 7 pages.
Non Final Office Action received for U.S. Appl. No. 11/901,336, dated Apr. 27, 2010, 10 pages.
Notice of Allowance received for U.S. Appl. No. 11/901,336, dated Aug. 24, 2010, 5 pages.
Official Communication pursuant to Article 94(3) EPC received for European Patent Application No. 11162906.9, dated Mar. 6, 2013, 5 pages.
Official Communication pursuant to Rules 161(2) and 162 EPC received for European Patent Application No. 11772569.7, dated Nov. 30, 2012, 2 pages.
Extended European Search Report received for European Patent Application No. 11850707.8, dated Jul. 3, 2014, 8 pages.
Non Final Office Action received for U.S. Appl. No. 12/214,687, dated Jun. 2, 2011, 5 pages.
Non Final Office Action received for U.S. Appl. No. 12/226,763, dated Aug. 22, 2011, 13 pages.
Final Office Action received for U.S. Appl. No. 12/226,763, dated Jan. 10, 2012, 16 pages.
Notice of Allowance received for U.S. Appl. No. 12/226,763, dated May 29, 2012, 9 pages.
Notice of Allowance received for U.S. Appl. No. 12/226,763, dated Oct. 1, 2012, 7 pages.
Notice of Allowance received for U.S. Appl. No. 12/226,763, dated Jan. 22, 2013, 7 pages.
Non Final Office Action received for U.S. Appl. No. 12/229,225, dated Aug. 16, 2011, 6 pages.
Final Office Action received for U.S. Appl. No. 12/229,225, dated Jan. 6, 2012, 7 pages.
Non Final Office Action received for U.S. Appl. No. 12/286,913, dated Sep. 28, 2011, 7 pages.
Non Final Office Action received for U.S. Appl. No. 12/286,913, dated Mar. 1, 2012, 7 pages.
Notice of Allowance received for U.S. Appl. No. 12/286,913, dated Oct. 3, 2012, 8 pages.
Notice of Allowance received for U.S. Appl. No. 12/976,344, dated Feb. 23, 2012, 7 pages.
Notice of Allowance received for U.S. Appl. No. 12/976,344, dated Mar. 27, 2012, 8 pages.
Non-Final Office Action received for U.S. Appl. No. 12/976,344, dated Apr. 5, 2013, 12 pages.
Non-Final Office Action received for U.S. Appl. No. 12/976,344, dated Apr. 1, 2014, 19 pages.
Notice of Allowance received for U.S. Appl. No. 12/976,344, dated Nov. 28, 2014, 11 pages.
Restriction Requirement received for U.S. Appl. No. 13/202,011, dated Jul. 17, 2012, 6 pages.
Non Final Office Action received for U.S. Appl. No. 13/202,011, dated Sep. 27, 2012, 8 pages.
Notice of Allowance received for U.S. Appl. No. 13/202,011, dated Apr. 9, 2013, 9 pages.
Notice of Allowance received for U.S. Appl. No. 13/202,011, dated Nov. 8, 2013, 7 pages.
Non Final Office Action received for U.S. Appl. No. 13/591,092, dated Dec. 13, 2012, 13 pages.
Final Office Action received for U.S. Appl. No. 13/591,092, dated Mar. 25, 2013, 22 pages.
Advisory Action received for U.S. Appl. No. 13/591,092, dated Jun. 6, 2013, 3 pages.
Notice of Allowance received for U.S. Appl. No. 13/591,092, dated Feb. 21, 2014, 11 pages.
Restriction Requirement received for U.S. Appl. No. 13/997,043, dated Jan. 23, 2015, 11 pages.
Office Action received for Mexican Patent Application No. MX/a/2011/012357, dated Mar. 13, 2013, 1 page of "Unofficial" English Translation.
Office Action received for Canadian Patent Application No. 2,650,860, dated May 12, 2011, 2 pages.
Office Action received for Canadian Patent Application No. 2,650,860 dated Jun. 18, 2012, 2 pages.

(56) References Cited

OTHER PUBLICATIONS

Notice of Allowance received for Canadian Patent Application No. 2,650,860, dated Apr. 2, 2013, 1 page.
Office Action received for Canadian Patent Application No. 2,650,860, dated Oct. 24, 2011, 3 pages.
Office Action received for Canadian Patent Application No. 2,737,704, dated Jun. 4, 2012, 4 pages.
Office Action received for Canadian Patent Application No. 2,737,704, dated Nov. 5, 2012, 3 pages.
Office Action received for Canadian Patent Application No. 2,737,704, dated Feb. 21, 2013, 3 pages.
Office Action received for Canadian Patent Application No. 2,760,840, dated Mar. 28, 2012, 3 pages.
Office Action received for Canadian Patent Application No. 2,760,840, dated Aug. 6, 2012, 4 pages.
Office Action received for Canadian Patent Application No. 2,760,840, dated Jan. 3, 2013, 3 pages.
Office Action received for Canadian Patent Application No. 2,760,840, dated Jul. 30, 2013, 4 pages.
Office Action received for Canadian Patent Application No. 2,762,985 dated Mar. 13, 2012, 4 pages.
Office Action received for Canadian Patent Application No. 2,762,985, dated Jul. 6, 2012, 2 pages.
Office Action received for Chinese Patent Application No. 200780025394.4, dated Oct. 13, 2011, 7 pages of English Translation and 4 pages of Official Copy.
Office Action received for Chinese Patent Application No. 200780025394.4, dated Oct. 30, 2012, 2 pages of English Translation and 3 pages of Official Copy.
Patent Examination Report received for Australian Patent Application No. 2010249409, dated Aug. 30, 2012, 4 pages.
Patent Examination Report received for Australian Patent Application No. 2011201768, dated Jun. 21, 2012, 3 pages.
Patent Examination Report received for Australian Patent Application No. 2011348161, dated Feb. 21, 2014, 4 pages.
Office Action received for Chinese Patent Application No. 201210287568.7, dated Jul. 12, 2013, 2 pages of English Translation and 5 pages of Official Copy.
Notice of Allowance received for U.S. Appl. No. 13/458,830, dated Jul. 9, 2014, 8 pages.
Patent Examination Report received for Australian Patent Application No. 2007248736, dated Dec. 1, 2009, 2 pages.
Office Action received for Indian Patent Application No. 5933/CHENP/2008, dated Oct. 29, 2010, 2 pages.
International Search Report and Written Opinion received for PCT Patent Application No. PCT/US2007/010410, dated Jun. 10, 2008, 5 pages.
International Preliminary Report on Patentability received for PCT Patent Application No. PCT/US2007/010410, dated Dec. 12, 2008, 5 pages.
International Search Report and Written Opinion received for PCT Patent Application No. PCT/US2007/010415, dated Oct. 11, 2007, 5 pages.
International Preliminary Report on Patentability received for PCT Patent Application No. PCT/US2007/010415, dated Aug. 5, 2008, 6 pages.
International Search Report and Written Opinion received for PCT Patent Application No. PCT/US2008/011488, dated Jan. 8, 2009, 6 pages.
International Search Report and Written Opinion received for PCT Application No. PCT/US2010/046525, dated Apr. 29, 2011, 9 pages.
International Preliminary Report on Patentability received for PCT Patent Application No. PCT/US2010/046525, dated Feb. 28, 2012, 5 pages.
International Search Report and Written Opinion received for PCT Patent Application No. PCT/US2011/061617, dated Jun. 8, 2012, 10 pages.
International Search Report and Written Opinion received for PCT Patent Application No. PCT/US2011/066868, dated Sep. 19, 2012, 6 pages.
International Preliminary Report on Patentability received for PCT Application No. PCT/US2011/066868, dated Jul. 4, 2013, 5 pages.
International Search Report and Written Opinion received for PCT Application No. PCT/US2012/059898, dated Jul. 26, 2013, 11 pages.
International Search Report and Written Opinion received for PCT Patent Application No. PCT/US2013/028689, dated Jun. 4, 2013, 5 pages.
International Search Report received for PCT Patent Application No. PCT/US2013/037935, dated Jul. 19, 2013, 4 pages.
Adapa et al., "Compression Characteristics of Selected Ground Agricultural Biomass", Agricultural Engineering International: the CIGR Ejournal. Manuscript 1347, vol. XI, Jun. 2009, 19 pages.
Adapa et al., "Pelleting Characteristics of Selected Biomass with and without Steam Explosion Pretreatment", Internation Journal of Agricultural and Biological Engineering, vol. 3, No. 3, Sep. 2010, pp. 62-79.
Alizadeh et al., "Pretreatment of Switchgrass by Ammonia Fiber Explosion (AFEX)", Applied Biochemistry and Biotechnology, vol. 121-124, 2005, pp. 1133-1141.
Allan et al., "Replacement of Fish Meal in Diets for Australian Silver Perch, *Bidyanus bidyanus*: I. Digestibility of Alternative Ingredients", Aquaculture, vol. 186, No. 3-4, Jun. 2000, pp. 293-310.
Balan et al., "Lignocellulosic Biomass Pretreatment Using AFEX", Biofuels: Methods and Protocols, Methods in Molecular Biology, Chapter 5, vol. 581, 2009, pp. 61-77.
Balan et al., "Mushroom Spent Straw: A Potential Substrate for an Ethanol-Based Biorefinery", Journal of Industrial Microbiology and Biotechnology, vol. 35, No. 5, 2008, pp. 293-301.
Baldrian et al., "Variability of Laccase Activity in the White-Rot Basidiomycete *Pleurotus ostreatus*", Folia Microbiologica, vol. 47, No. 4, 2002, pp. 385-390.
Bals et al., "Enzymatic Hydrolysis of Distiller's Dry Grain and Solubles (DDGS) Using Ammonia Fiber Expansion Pretreatment", Energy and Fuels, vol. 20, No. 6, Oct. 2006, pp. 2732-2736.
Bals et al., "Evaluating the Impact of Ammonia Fiber Expansion (AFEX) Pretreatment Conditions on the Cost of Ethanol Production", Bioresource Technology, vol. 102, 2011, pp. 1277-1283.
Beale et al., "Leaf Photosynthesis in the C4-Grass Miscanthus x giganteus, Growing in the Cool Temperate Climate of Southern England", Journal of Experimental Botany, vol. 47, No. 295, Feb. 1996, pp. 267-273.
Belyea et al., "Element Concentrations of Dry-Grind Corn-Processing Streams", Applied Biochemistry and Biotechnology, vol. 134, No. 2, 2006, pp. 113-128.
Bergner et al., "Archives of Animal Nutrition", Arch. Tierernahr, vol. 30, 1980, pp. 239-256.
Betschart et al., "Extractability and Solubility of Leaf Protein", Journal of Agricultural and Food Chemistry, vol. 21, No. 1, 1973, pp. 60-65.
Boluk, Yaman, "Acid-Base Interactions and Swelling of Cellulose Fibers in Organic Liquids", Cellulose, vol. 12, No. 6, Dec. 2005, pp. 577-593.
Bothast et al., "Biotechnological Processes for Conversion of Corn into Ethanol", Applied Microbiology and Biotechnology, vol. 67, No. 1, Apr. 2005, pp. 19-25.
Carolan et al., "Technical and Financial Feasibility Analysis of Distributed Bioprocessing Using Regional Biomass Pre-Processing Centers", Journal of Agricultural and Food Industrial Organization, vol. 5, No. 2, Article 10, 2007, 29 pages.
Cen et al., "Production of Cellulase by Solid-State Fermentation", Advances in Biochemical Engineering/ Biotechnology, vol. 65, 1999, pp. 69-92.
Chahal, D. S., "Bioconversion of Hemicelluloses into Useful Products in an Integrated Process for Food/Feed and Fuel (Ethanol) Production form Biomass", Biotechnology and Bioengineering Symposium, No. 14, 1984, pp. 425-433.

(56) References Cited

OTHER PUBLICATIONS

Chahal et al., "Production of Cellulase in Solid-State Fermentation with Trichoderma reesei MCG 80 on Wheat Straw", Applied Biochemistry and Biotechnology, vol. 57/58, 1996, pp. 433-442.

Chang, Shu-Ting, "The World Mushroom Industry: Trends and Technological Development", International Journal of Medicinal Mushrooms, vol. 8, 2006, pp. 297-314.

Christian et al., "Degradation of Xenobiotic Compounds by Lignin-Degrading White-Rot Fungi: Enzymology and Mechanisms Involved", Indian Journal of Experimental Biology, vol. 43, Apr. 2005, pp. 301-312.

Chundawat et al., "Effect of Particle Size Based Separation of Milled Corn Stover on AFEX Pretreatment and Enzymatic Digestibility", Biotechnology and Bioengineering, vol. 96, No. 2, Feb. 1, 2007, pp. 219-231.

Chundawat et al., "Multi-scale Visualization and Characterization of Lignocellulosic Plant Cell Wall Deconstruction During Thermochemical Pretreatment", Energy & Environmental Science, No. 4, 2011, pp. 973-984.

Chundawat, Shishir P.S., "Ultrastructural and Physicochemical Modifications within Ammonia Treated Lignocellulosic Cell Walls and their Influence on Enzymatic Digestibility", Dissertation for Michigan State University, vol. 1, 2010, 230 pages.

Clifton-Brown et al., "Performance of 15 Miscanthus Genotypes at Five Sites in Europe", Agronomy Journal, vol. 93, No. 5, 2001, pp. 1013-1019.

Cohen et al., "Biotechnological Applications and Potential of Wood-Degrading Mushrooms of the Genus *Pleurotus*", Applied Microbiology and Biotechnology, vol. 58, Feb. 2002, pp. 582-591.

Cosgrove, Daniel J., "Growth of the Plant Cell Wall", Nature Reviews, Molecular Cell Biology, vol. 6, Nov. 2005, pp. 850-861.

Dale et al., "Extrusion Processing for Ammonia Fiber Explosion (AFEX)", Applied Biochemistry and Biotechnology, vol. 77-79, 1999, pp. 35-45.

Dale et al., "Fermentation of Lignocellulosic Materials Treated by Ammonia Freeze-Explosion", Developments in Industrial Microbiology, 1985, pp. 223-233.

Eggeman, T., "Boundary Analysis for H2 Production by Fermentation", National Renewable Energy Laboratory, Subcontract Report NREL/SR-560-36129, May 2005, 17 pages.

El-Adawy et al., "Nutritional Potential and Functional Properties of Sweet and Bitter Lupin Seed Protein Isolates", Food Chemistry, vol. 74, No. 4, 2001, pp. 455-462.

"Energy Policy Act of 2005", Public Law 109-58, 119 Stat. 1067, Aug. 8, 2005, 11 pages.

Erickson, David R., "Edible Fats and Oils Processing—Basic Principles and Modern Practices", World Conference Proceedings, AOCS Press, Netherlands, 1990, 6 pages.

Renewals Fuels Association, "U.S. Fuel Ethanol Industry Biorefineries and Production Capacity, RFA—The Industry—Plant Locations", available online at <http://http://www.ethanolrfa.org/biorefinery-locations/, prior to Sep. 2, 2014, 4 pages.

Felix et al., "In Vitro and in Vivo Digestibility of Soya-Bean Straw Treated with Various Alkalis", Animal Production, vol. 51, No. 1, 1990, pp. 47-59.

Fernandez et al., "Protein Extraction from Atriplex lampa Leaves: Potential Use as Forage for Animals used for Human Diets", Plant Foods for Human Nutrition, vol. 54, No. 3, 1999, pp. 251-259.

Ferrer et al., "Increasing Nutrient Availability of Feather Meal for Ruminants and Non-Ruminants Using an Ammonia Pressurisation/Depressurisation Process", Journal of the Science of Food and Agriculture, vol. 79, 1999, pp. 828-832.

Ferrer et al., "NR 06. Sugar Production from Rice Straw", Archivos Latinoamericanos de Produccion Animal, vol. 5, No. 1, 1997, pp. 112-114.

Ferrer et al., "Optimizing Ammonia Pressurization/Depressurization Processing Conditions to Enhance Enzymatic Susceptibility of Dwarf Elephant Grass", Applied Biochemistry and Biotechnology, vol. 84-86, No. 1-9, Mar. 2000, pp. 163-179.

Fiorentini et al., "Protein Concentrate", Journal of Food Science, vol. 46, No. 5, Sep. 1981, pp. 1514-1517.

Foster et al., "Enzymatic Hydrolysis of Ammonia-Treated Sugar Beet Pulp", Applied Biochemistry and Biotechnology, vol. 91-93, 2001, pp. 269-282.

Gao et al., "Mixture Optimization of Six Core Glycosyl Hydrolases for Maximizing Saccharification of Ammonia Fiber Expansion (AFEX) Pretreated Corn Stover", Bioresource Technology, vol. 101, No. 8, Apr. 2010, pp. 2770-2781.

Gollapalli et al., "Predicting Digestibility of Ammonia Fiber Explosion (AFEX)-Treated Rice Straw", Applied Biochemistry and Biotechnology, vol. 98-100, 2002, pp. 23-35.

Gray et al., "Bioethanol", Current Opinion in Chemical Biology, vol. 10, 2006, pp. 141-146.

Greene et al., "Growing Energy—How Biofuels Can Help End America's Oil Dependence", Natural Resources Defense Council, Dec. 2004, 86 pages.

Hahn-Hagerdal et al., "Bio-Ethanol—the Fuel of Tomorrow from the Residues of Today", Trends in Biotechnology, vol. 24, No. 12, Dec. 2006, pp. 549-556.

Hanchar et al., "Separation of Glucose and Pentose Sugars by Selective Enzyme Hydrolysis of AFEX-Treated Corn Fiber", Applied Biochemistry and Biotechnology, vol. 136-140, No. 1-12, 2007, pp. 313-325.

Heaton et al., "A Quantitative Review Comparing the Yields of Two Candidate C4 Perennial Biomass Crops in Relation to Nitrogen, Temperature and Water", Biomass and Bioenergy, vol. 27, No. 1, Jul. 2004, pp. 21-30.

Heaton et al., "Miscanthus for Renewable Energy Generation: European Union Experience and Projections for Illinois", Mitigation and Adaptation Strategies for Global Change, vol. 9, No. 4, Oct. 2004, pp. 433-451.

Holtzapple et al., "The Ammonia Freeze Explosion (AFEX) Process—A Practical Lignocellulose Pretreatment", Applied Biochemistry and Biotechnology, vol. 28/29, No. 1, 1991, pp. 59-74.

Houghton et al., "Fungal Upgrading of Wheat Straw for Straw-Thermoplastics Production", Applied Biochemistry and Biotechnology, vol. 113-116, 2004, pp. 71-93.

Jain et al., "Effect of Ammonia Pretreatment on Switchgrass for Production of Cellulase using Trichoderma reesei Rut C-30", 31st Symposium on Biotechnology for Fuels and Chemicals, May 3-6, 2009, 1 page.

Jeoh et al., "Cooperative and Competitive Binding in Synergistic Mixtures of Thermobifida fusca Cellulases Cel5A, Cel6B, and Cel9A", Biotechnology Progress, vol. 18, No. 4, 2002, pp. 760-769.

Jin et al., "A Novel Integrated Biological Process for Cellulosic Ethanol Production Featuring High Ethanol Productivity, Enzyme Recycling and Yeast Cells Reuse", Energy & Environmental Science, No. 5, 2012, 8 pages.

Jin et al., "Two-Step SSCF to Convert AFEX-Treated Switchgrass to Ethanol using Commercial Enzymes and *Saccharomyces cerevisiae* 424A (LNH-ST)", Bioresource Technology, vol. 101, No. 21, 2010, pp. 8171-8178.

Kaliyan et al., "Roll Press Briquetting and Pelleting of Corn Stover and Switchgrass", Transactions of the ASABE, vol. 52, No. 2, © 2009, pp. 543-555.

Kamm et al., "Principles of Biorefineries", Applied Microbiology and Biotechnology, vol. 64, No. 2, Apr. 2004, pp. 137-145.

Kim et al., "Enhancement of the Enzymatic Digestibility of Waste Newspaper Using Tween", Applied Biochemistry and Biotechnology, vol. 129-132, 2006, pp. 486-495.

Kim et al., "Lime Pretreatment and Enzymatic Hydrolysis of Corn Stover", Bioresource Technology, vol. 96, No. 18, 2005, pp. 1994-2006.

Kim et al., "Pretreatment and Fractionation of Corn Stover by Ammonia Recycle Percolation Process", Bioresource Technology, vol. 96, No. 18, 2005, pp. 2007-2013.

Kim et al., "Pretreatment of Corn Stover by Low-Liquid Ammonia Recycle Percolation Process", Applied Biochemistry and Biotechnolology, vol. 133, Apr. 2006, pp. 41-57.

Knauf et al., "Lignocellulosic Biomass Processing: A Perspective", International Sugar Journal, vol. 106, No. 1263, 2004, pp. 147-150.

(56) References Cited

OTHER PUBLICATIONS

Kudra et al., "Advanced Drying Technologies: Superheated Steam Drying", Chapter 7, Marcel Dekker, Inc.,2002, pp. 81-111.

Kumar et al., "Does Densification Influence the Steam Pretreatment and Enzymatic Hydrolysis of Softwoods to Sugars?", Bioresource Technology, vol. 121, Oct. 2012, 38 pages.

Kumar et al., "Methods for Pretreatment of Lignocellulosic Biomass for Efficient Hydrolysis and Biofuel Production", Industrial and Engineering Chemistry Research, 2009, pp. A-Q.

Ladisch et al., "Building a Bridge to the Ethanol Industry—Follow-Up Project", National Renewable Energy Laboratory, Subcontractor Report NREL/SR-510-33894, Apr. 2003, 36 pages.

Advisory Action received for U.S. Appl. No. 14/251,921, dated Jul. 18, 2017, 4 pages.

Final Office Action received for U.S. Appl. No. 14/251,921, dated Apr. 4, 2017, 13 pages.

Non-Final Office Action received for U.S. Appl. No. 14/251,921, dated Oct. 4, 2017, 15 pages.

Notice of Allowance received for Canada Patent Application No. 2,870,758, dated Sep. 12, 2017, 1 page.

Decision of Rejection received for Chinese Patent Application No. 201380022053.7, dated Jul. 19, 2017 (8 pages of English Translation and 7 pages of Official Copy).

Notice of Allowance Received for Japanese Patent Application No. 2015-509190, dated Oct. 24, 2017, 4 pages.

\* cited by examiner

METHODS FOR INCREASING SUGAR YIELD WITH SIZE-ADJUSTED LIGNOCELLULOSIC BIOMASS PARTICLES

This application is a U.S. National Stage Filing under 35 U.S.C. 371 from International Application No. PCT/US2013/028689, having an International Filing Date of Mar. 1, 2013 and published in English as WO2013/131015 on Sep. 6, 2013, which application claims the benefit under 35 U.S.C. 119 (e) of U.S. Provisional Application Ser. No. 61/606,139 filed on Mar. 2, 2012 (hereinafter "'139 Application"), which is hereby incorporated by reference herein in its entirety.

STATEMENT OF GOVERNMENT RIGHTS

This invention was made with government support under DE-FC02-07ER64494 awarded by the U.S. Department of Energy. The government has certain rights in this invention.

BACKGROUND

Biofuels produced today are based on corn and other grains, transesterified biodiesel from oilseed crops, such as soybeans and animal fats. Ethanol production from grains is currently the mainstay of the domestic ethanol industry. However, there is increasing demand for cellulosic-based biofuels. Lignocellulosic biomass (LCB) is a promising feedstock, as it is a readily-available low cost feedstock and is expected to reduce greenhouse gas emissions.

SUMMARY

There is a need for improving digestibility of lignocellulosic biomass (LCB) to improve downstream sugar yield. In one embodiment, a method for size-adjusting LCB particles for use as feedstock for a pretreatment process is provided. In one embodiment, a LCB particle is size-adjusted in a manner that produces particles having an average particle size less than particles produced in a conventional size-adjusting process. In one embodiment, a resulting LCB particle has an average particle size greater than 5 mm in at least one direction.

In one embodiment, a plurality of LCB particles is provided, having an average particle size between about 1 cm and about 5 cm in at least one dimension.

In one embodiment, a method of increasing sugar yield in a bio-product production process is provided, comprising pretreating one or more size-adjusted LCB particles having an average particle size greater than 5 mm in at least one dimension with an ammonia pretreatment, such as a gaseous ammonia pretreatment. In one embodiment, the ammonia pretreatment can be performed above the glass transition temperature of the LCB particle (high severity).

The use of a protocol which, in one embodiment, finely tunes the size of the starting LCB particles to a size which can be orders of magnitude higher than conventional particles, in order to optimize downstream sugar yields, represents a paradigm shift in the previously understood need to reduce LCB particles down to fine sizes, such as to an average particle size of 5 mm or less. In one embodiment, surprisingly, use of LCB particles larger than 5 mm, such as up to 5 cm or larger, improves sugar yield downstream, as compared with sugar yields using particle sizes 5 mm or smaller. An improved sugar yield can, in turn, improve production yields of various bio-products. As such, in one embodiment, the methods described herein demonstrate an improvement to the efficiency and economy of producing bio-products such as cellulosic biofuels.

DETAILED DESCRIPTION

Figure 1:
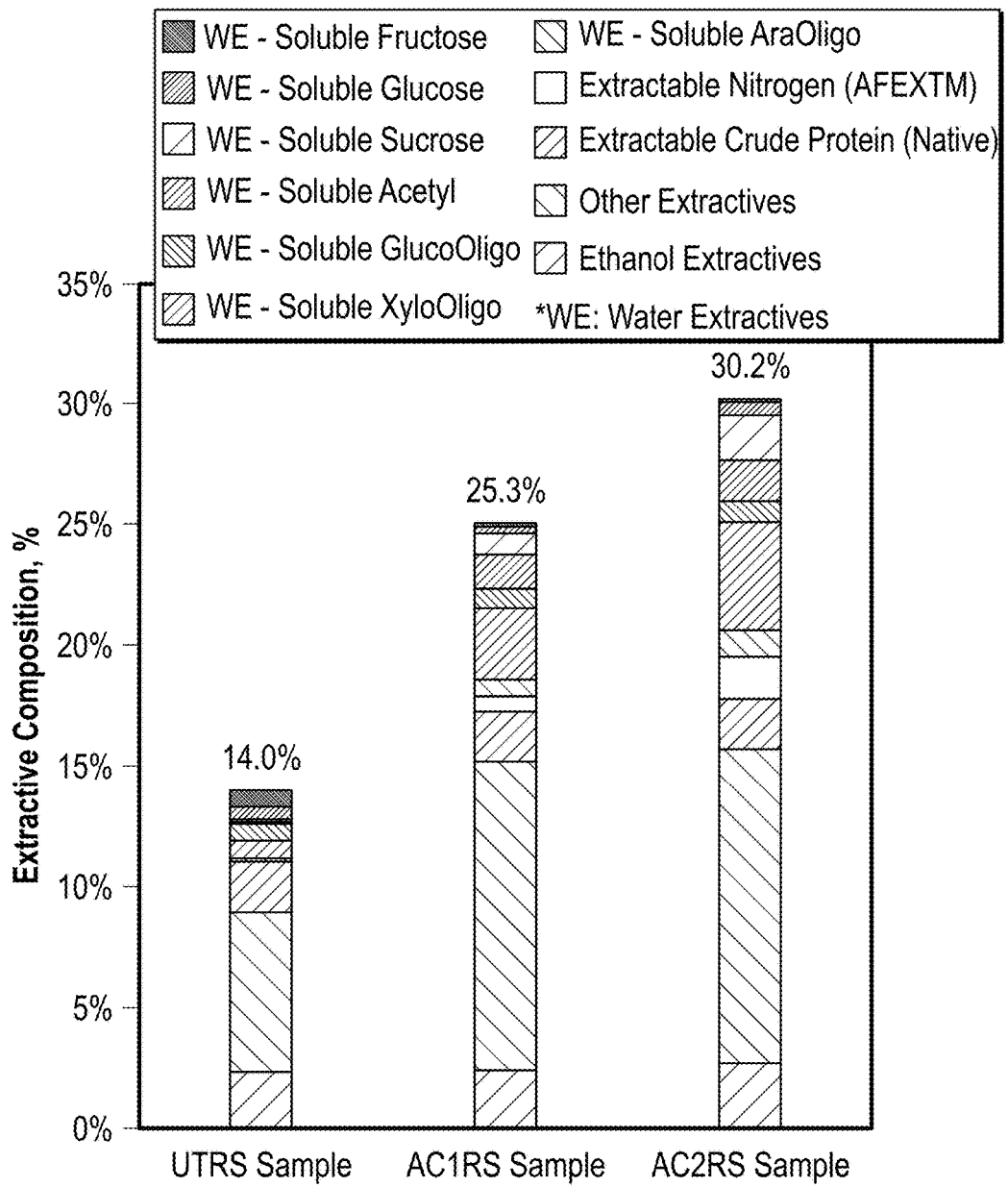
FIG. 1 is a graph showing the extractive composition for untreated rice straw (URS), AFEX™ treated rice straw under "C1" conditions of 100° C.; 2:1 ammonia to biomass ratio, 80% moisture and 30 minutes residence time (hereinafter referred to as "AC1RS") and AFEX™ treated rice straw under "C2" conditions of 140° C.; 1:1 ammonia to biomass ratio, 130% moisture and 50 minutes residence time (hereinafter referred to as "AC2RS") according to various embodiments.

In the following detailed description of embodiments of the invention, embodiments are described in sufficient detail to enable those skilled in the art to practice them, and it is to be understood that other embodiments may be utilized and that chemical and procedural changes may be made without departing from the spirit and scope of the present subject matter. The following detailed description is, therefore, not to be taken in a limiting sense, and the scope of embodiments of the present invention is defined only by the appended claims.

The term "biomass" as used herein, refers in general to organic matter harvested or collected from a renewable biological resource as a source of energy. The renewable biological resource can include plant materials, animal materials, and/or materials produced biologically. The term "biomass" is not considered to include fossil fuels, which are not renewable.

The term "plant biomass" or "ligno-cellulosic biomass (LCB)" as used herein is intended to refer to virtually any plant-derived organic matter containing cellulose and/or hemicellulose as its primary carbohydrates (woody or non-woody) available for energy on a renewable basis. Plant biomass can include, but is not limited to, agricultural residues such as corn stover, wheat straw, rice straw, sugar cane bagasse and the like. Plant biomass further includes, but is not limited to, woody energy crops, wood wastes and residues such as trees, including fruit trees, such as fruit-bearing trees, (e.g., apple trees, orange trees, and the like), softwood forest thinnings, barky wastes, sawdust, paper and pulp industry waste streams, wood fiber, and the like. Additionally perennial grass crops, such as various prairie grasses, including prairie cord grass, switchgrass, *Miscanthus*, big bluestem, little bluestem, side oats grama, and the like, have potential to be produced large-scale as additional plant biomass sources. For urban areas, potential plant biomass feedstock includes yard waste (e.g., grass clippings, leaves, tree clippings, brush, etc.) and vegetable processing waste. Plant biomass is known to be the most prevalent form of carbohydrate available in nature and corn stover is currently the largest source of readily available plant biomass in the United States. When used without a qualifier, the term "biomass" is intended to refer to LCB.

The term "biofuel" as used herein, refers to any renewable solid, liquid or gaseous fuel produced biologically and/or chemically, for example, those derived from biomass. Most biofuels are originally derived from biological processes such as the photosynthesis process and can therefore be considered a solar or chemical energy source. Other biofuels, such as natural polymers (e.g., chitin or certain sources of microbial cellulose), are not synthesized during photosynthesis, but can nonetheless be considered a biofuel because they are biodegradable. There are generally considered to be three types of biofuels derived from biomass synthesized during photosynthesis, namely, agricultural biofuels (defined below), municipal waste biofuels (residential and light commercial garbage or refuse, with most of the recyclable materials such as glass and metal removed) and forestry biofuels (e.g., trees, waste or byproduct streams from wood products, wood fiber, pulp and paper industries). Biofuels produced from biomass not synthesized during photosynthesis include, but are not limited to, those derived from chitin, which is a chemically modified form of cellulose known as an N-acetyl glucosamine polymer. Chitin is a significant component of the waste produced by the aquaculture industry because it comprises the shells of seafood.

The term "agricultural biofuel", as used herein, refers to a biofuel derived from agricultural crops, lignocellulosic crop residues, grain processing facility wastes (e.g., wheat/oat hulls, corn/bean fines, out-of-specification materials, etc.), livestock production facility waste (e.g., manure, carcasses, etc.), livestock processing facility waste (e.g., undesirable parts, cleansing streams, contaminated materials, etc.), food processing facility waste (e.g., separated waste streams such as grease, fat, stems, shells, intermediate process residue, rinse/cleansing streams, etc.), value-added agricultural facility byproducts (e.g., distiller's wet grain (DWG) and syrup from ethanol production facilities, etc.), and the like. Examples of livestock industries include, but are not limited to, beef, pork, turkey, chicken, egg and dairy facilities. Examples of agricultural crops include, but are not limited to, any type of non-woody plant (e.g., cotton), grains such as corn, wheat, soybeans, sorghum, barley, oats, rye, and the like, herbs (e.g., peanuts), short rotation herbaceous crops such as switchgrass, alfalfa, and so forth.

The term "pretreatment step" as used herein, refers to any step intended to alter native biomass so it can be more efficiently and economically converted to reactive intermediate chemical compounds such as sugars, organic acids, etc., which can then be further processed to a variety of end products such as ethanol, iso-butanol, long chain alkanes etc. Pretreatment can reduce the degree of crystallinity of a polymeric substrate, reduce the interference of lignin with biomass conversion and prehydrolyze some of the structural carbohydrates, thus increasing their enzymatic digestibility and accelerating the degradation of biomass to useful products. Pretreatment methods can utilize acids of varying concentrations, including dilute acid pretreatments, concentrated acid pretreatments (using, for example, sulfuric acids, hydrochloric acids, organic acids, and the like) and/or alkali such as ammonia, ammonium hydroxide, sodium hydroxide, lime, and the like. Pretreatment methods can additionally or alternatively utilize hydrothermal treatments including water, heat, steam or pressurized steam pretreatments, including, but not limited to, hydro-thermolysis pretreatment and liquid hot water pretreatment, further including, for example, acid catalyzed steam explosion pretreatment. Pretreatment can occur or be deployed in various types of containers, reactors, pipes, flow through cells and the like. Most pretreatment methods will cause the partial or full solubilization and/or destabilization of lignin and/or hydrolysis of hemicellulose to pentose sugars. Further examples of pretreatment include, but are not limited wet oxidation, organosolv pretreatment and mechanical extrusion.

The term "Ammonia Fiber Expansion" (hereinafter "AFEX™") pretreatment" as used herein, refers to a process for pretreating biomass with liquid and/or vapor ammonia (i.e., gaseous ammonia pretreatment (GAP) to solubilize lignin and redeposit it from interior of plant cell walls to the surface of the biomass. An AFEX™ pretreatment disrupts the lignocellulosic matrix, thus modifying the structure of lignin, partially hydrolyzing hemicellulose, and increasing the accessibility of cellulose and the remaining hemicellulose to subsequent enzymatic degradation. Lignin is a primary impediment to enzymatic hydrolysis of native biomass, and removal or transformation of lignin is a suspected mechanism of several of the leading pretreatment technologies, including AFEX™. The process further expands and swells cellulose fibers and further breaks up amorphous hemicellulose in LCB. These structural changes open up the plant cell wall structure enabling more efficient and complete conversion of LCB to value-added products while preserving the nutrient value and composition of the material. Modified AFEX™ pretreatments further include, for example extractive AFEX™ (E-AFEX™).

The term "Klason lignin" as used herein refers to insoluble lignin obtained from LCB after the soluble lignin components of the LCB have been removed with a prescribed dilute sulfuric acid treatment.

The term "glass transition temperature" as used herein refers to abrupt softening of lignin in LCB at a particular temperature or over relatively narrow ranges of temperature. When lignin softens up, the ammonia helps to break hemicellulose-lignin ester linkages in LCB particles. A glass transition temperature can be reached during a pretreatment process, such as an ammonia pretreatment process.

The term "low severity pretreatment conditions" as used herein, refers to pretreatment conditions in which the temperature of the LCB particles, i.e., the reaction temperature, is below the glass transition temperature of the LCB particles being treated.

The term "high severity pretreatment conditions" as used herein, refers to pretreatment conditions in which the temperature of the LCB particles, i.e., the reaction temperature, is greater than the glass transition temperature of the LCB particles being treated.

The term "moisture content" as used herein, refers to the quantity of water in biomass. Moisture content is usually expressed on a dry weight basis (dwb) as follows: $MC_{dwb} = \{(W_i - W_f)/W_f\}*100$ wherein $W_i$ is the initial weight of biomass before drying and $W_f$ is the final weight of biomass after drying.

The term "particle" as used herein refers to an individual piece of biomass, such as LCB (i.e., an "LCB particle"). A LCB is useful as a starting material for various biofuel production processes and can include an "as is" harvested piece of biomass (whole biomass) or a size-adjusted piece of biomass (after milling or chopping). When used without qualification, the term "particle" is intended to refer to an "LCB particle."

The term "substrate" as used herein refers to a collection of LCB particles. The particles of a given substrate are generally similar in size, although can include slight variations in particle size distribution, such that the "size" which is noted herein is intended to be a reference to an average particle size.

The major structural components of biomass feedstocks are cellulose (glucan), lignin (Klason lignin, acid soluble lignin), hemicellulose (primarily made up of xylan) and ash. Other sugars that make up the structural component are galactan, arabinan and mannan. Non-structural components of LCB that are generally measured are extractives and proteins.

Nearly all forms of ligno-cellulosic biomass, i.e., plant biomass, such as monocots, comprise three primary chemical fractions: hemicellulose, cellulose, and lignin. Hemicellulose is a polymer of short, highly-branched chains of mostly five-carbon pentose sugars (xylose and arabinose), and to a lesser extent six-carbon hexose sugars (galactose, glucose and mannose). Dicots, on the other hand, have a high content of pectate and/or pectin, which is a polymer of alpha-linked glucuronic acid. Pectate may be "decorated" with mannose or rhamnose sugars, also). Some of these sugars are acetylated.

Because of its branched structure, hemicellulose is amorphous and relatively easy to hydrolyze (breakdown or cleave) to its individual constituent sugars by enzyme or dilute acid treatment. Cellulose is a linear polymer of glucose sugars, much like starch, which is the primary substrate of corn grain in dry grain and wet mill ethanol plants. However, unlike starch, the glucose sugars of cellulose are strung together by β-glycosidic linkages which allow cellulose to form closely-associated linear chains. Because of the high degree of hydrogen bonding that can occur between cellulose chains, cellulose forms a rigid crystalline structure that is highly stable and much more resistant to hydrolysis by chemical or enzymatic attack than starch or hemicellulose polymers.

Hemicelluloses of rice straw comprise primarily α-L-(1-3)-arabino-(4-O-methyl-α-(1-2)-D-glucurono)-β-(1-4)-D-xylan and arabino-glucuronoxylan, (AGX). Xylan backbone β-(1-4)-D-xylopyranosyl units are substituted by monomeric 4-O-methyl-α-D-glucopyranosyluronic acid residue (4-O-MeGlcA) and a α-L-arabinofuranosyl unit at the C2 and/or C3 main chain. A significant portion of the xylose in cereal straw cell walls was also acetylated, primarily on C2 and C3, with the acetyl group accounting for about 1 to about 5% (by weight) of the total LCB.

Lignin provides structural integrity to plants, and remains as residual material after the sugars in plant biomass have been fermented to ethanol. Lignin exists in plant tissue as a polymer of phenolic molecules, and is associated with cellulose, hemicelluloses and other polymers as lignin-carbohydrates complexes (LCCs) through covalent bonds. In herbaceous plants such as rice straw, LCCs contain ferulic bridges which are attached to lignin and carbohydrates (AGX) via ether and ester bonds, respectively. Alkali cleaves the ester bond components of such bridges, liberating the ferulic acid (FA) residue and lignin from carbohydrates and yielding a small amount of FA (1-4%). Isolated LCCs from rice straw is known to contain about 64% carbohydrates, about 3% uronic acid, about 33% lignin, about 4% acetyl groups, 4% trans-p-coumaric acid and about 1% trans-ferulic acid. Typical ranges of hemicellulose, cellulose, and lignin concentrations in plants are shown in Pauly, M., et. al., *Plant cell wall polymers as precursors for biofuels*, Curr Opin Plant Biol. June 2010: 13(3):305-12. Typically, cellulose makes up 30 to 50% of residues from agricultural, municipal, and forestry sources. While cellulose is more difficult to convert to ethanol than hemicellulose, it is the sugar polymers of hemicellulose which can be more readily hydrolyzed to their individual component sugars for subsequent fermentation to ethanol. Although hemicellulose sugars represent the "low-hanging" fruit for conversion to ethanol, the substantially higher content of cellulose represents the greater potential for maximizing alcohol yields, such as ethanol, on a per ton basis of plant biomass.

Therefore, a pretreatment process is used to alter and open up the cell wall matrix, to hydrolyze the hemicelluloses, and to reduce crystallinity. Ultimately, the pretreatment process makes the cellulose more accessible (during a subsequent enzyme hydrolysis process) for conversion of the carbohydrate polymer into fermentable sugars.

Conventional methods used to convert biomass to alcohol include processes employing a concentrated acid hydrolysis pretreatment, a two-stage acid hydrolysis pretreatment as well as processes employing any known conventional pretreatment, such as hydrothermal or chemical pretreatments, followed by an enzymatic hydrolysis (i.e., enzyme-catalyzed hydrolysis) or simultaneous enzymatic hydrolysis and saccharification. Such pretreatment methods can include, but are not limited to, dilute acid hydrolysis, high pressure hot water-based methods, i.e., hydrothermal treatments such as steam explosion and aqueous hot water extraction, reactor systems (e.g., batch, continuous flow, counter-flow, flow-through, and the like), AFEX™, ammonia recycled percolation (ARP), lime treatment and a pH-based treatment.

Several of these methods generate nearly complete hydrolysis of the hemicellulose fraction to efficiently recover high yields of the soluble pentose sugars. This also facilitates the physical removal of the surrounding hemicellulose and lignin, thus exposing the cellulose to later processing.

However, ammonia treatments, such as ammonia fiber expansion (AFEX™), are capable of opening up the cell wall in agricultural residues with greatly reduced degradation products, as compared to acidic pretreatments.

Various types of LCB can be used in the processes described herein, including, but not limited to, perennial and/or annual grasses (e.g., rice straw, *Micanthus*, switchgrass, sugar cane bagasse, wheat straw, Napier grass, *Erianthus*, empty fruit bunch from palm trees, and the like). Rice straw, for example, is one of the most plentiful LCB crop residues in the world. Approximately 60% of a rice crop production is rice straw, which is composed of leaf and sheath (53%), stem (44%) and panicles (3%) when cut at ground level. Many farmers openly burn rice straw to clean the rice field, as it offers a relatively inexpensive means of removing straw and clearing the rice field for subsequent planting. However, this option creates environmental, safety and health issues. As such, there is a need to find alternative ways to remove the rice straw after each harvesting season.

However, conversion of LCB, such as rice straw, to biofuel (e.g., ethanol) is more challenging than conversion of starchy materials, such as corn, due to the complex structure of the plant cell wall. Attempts to use rice straw and other LCB have, to date, focused on a perceived need to reduce the size of the LCB particle size to a magnitude of order of just a few millimeters or less (e.g., less than 5 mm), to improve the downstream sugar conversion rate. One goal of size reduction has been to reduce the crystallinity of the cellulose fibers in the biomass. Indeed, in addition to chemical pretreatment, such size reduction has heretofore been recommended as part of any physical pretreatment process for LCB particles. Size reduction of LCB particles to produce fine LCB particle sizes has also been thought to be necessary to eliminate the mass and heat transfer limitations during pretreatment and enzyme hydrolysis. Significant size reduction of harvested LCB particles, such as with reduction to particle sizes from 0.85-0.5 mm to <0.15 mm has been demonstrated to enhance glucan and xylan conversions by 15-20%. However, extensive size reduction is not only expensive, but can also cause significant carbohydrate losses, ultimately resulting in less sugar production and reduced ethanol yield.

The inventors have determined, surprisingly, and in contrast to conventional wisdom, that downstream sugar yield increases as the size (e.g., average size) of the starting material (LCB particles) is increased, when using a substrate containing LCB particles having a size greater than 5 mm in at least one dimension, as compared to LCB particles having a size of 5 mm or less in any dimension. This trend holds true for much larger LCB particles up to an order of magnitude larger in size, such as up to about 5 cm in at least one dimension, and likely is true for even larger LCB particles, such as up to 10 cm in at least one dimension, although the embodiments are not so limited. More specifically, when using a LCB substrate as a starting material for the production of bio-products, such as biofuel, together with a suitable pretreatment process, the resulting downstream sugar yield (monomeric and oligomeric sugars) increases. In one embodiment, the particles of a given substrate, which are generally similar in size, as noted in the definition, and can pass through an approximately 0.5 cm sieve when milling.

The total possible theoretical sugar yield for a given biomass is calculated based on the composition of glucan, xylan and arabinan present in biomass. To convert polymeric sugars to monomerics sugars, a multiple of 1.11 is used for glucan and 1.136 for xylan and arabinan. Therefore, the maximum theoretical sugar yield for rice straw is 639.1 g/kg of biomass for 100% conversion.

In one embodiment, sugar conversion using larger LCB particles is increased by at least 1% up to about 26% or higher, including any range or value therebetween, such as up to about 40% or higher. In one embodiment, sugar conversion is increased by at least 26%. For example, it is known that a conventional LCB particle size of 5 mm pretreated under AC2RS conditions (as defined herein) at 6% GL produces a sugar yield of 325 g/kg of biomass, i.e., a conversion of only 50%. In contrast, in one embodiment, the larger non-conventional LCB particle size of 5 cm in at least one dimension, when pretreated under AC2RS conditions at 6% GL hydrolysis surprisingly produces a much higher sugar yield of 486 g/kg, i.e., a conversion of 76%. This ability to convert 150 g/kg more from biomass to sugar represents a 26% increase.

In one embodiment, xylose yield is increased by at least 1% up to about 22%, including any range or value therebetween, or higher, depending on the particular LCB particle size or ratio of LCB particle sizes (between 5 mm and about 5 cm, including any range or value therebetween, or higher), the pretreatment conditions and the GL. In one embodiment, xylose yield is increased by at least or about 22%, again, depending on the particular LCB particle size or ratio of LCB particle sizes (between 5 mm and about 5 cm, including any range or value therebetween or higher), the pretreatment conditions and the GL.

In one embodiment, low severity pretreatment conditions, i.e., wherein the pretreatment reaction temperature is lower than the glass transition temperature of lignin present in LCB. However, the temperature and/or the residence time should not be so low as to cause an ineffective pretreatment step that would prevent or reduce the effectiveness of a subsequent hydrolysis step. In one embodiment, low severity pretreatment conditions include heating the LCB particles to a temperature less than or equal to 100° C. for a residence time of no more than or about 60 minutes.

In one embodiment, high severity pretreatment conditions, i.e., wherein the pretreatment reaction temperature is higher than the glass transition temperature of lignin present in LCB, are used.

In one embodiment, such conditions can include heating the LCB particles to a temperature of at least or above 120° C. for a residence time of at least or about 60 min.

Clearly, temperatures in between about 100° C. and about 160° C. can be used, as well as residence times between about 30 and about 60 minutes. Depending on the glass transition temperature of the LCB particles being treated, such a process can be either a low severity or high severity process.

In theory, to go beyond the glass transition temperature of lignin for a given LCB (at fixed ammonia loading and fixed moisture), one has to raise pretreatment temperature beyond a certain temperature range and maintain the conditions for certain residence time.

In one embodiment, the process operates under low severity pretreatment conditions for a period of time before operating under high severity pretreatment conditions. In one embodiment, the process is run under high severity pretreatment conditions for a period of time before being operated at low severity pretreatment conditions. In one embodiment, the process operates alternatively between low and high severity pretreatment conditions.

The glass transition temperature (Tg) of LCB varies depending on the composition of biomass, structure of lignin and ultra-structural network between lignin and hemicellulose. In one embodiment, the LCB is corn stover, and the lignin contained therein has a Tg of about 120° C. In one embodiment, the LCB is rice straw, and the lignin contained therein has a Tg of 140° C. In one embodiment, rice straw is subjected to a high severity AFEX™ pretreatment (>Tg), such as about 140° C., the extractability is higher as compared AFEX™ pretreatment done at 100° C. and untreated corn stover (FIG. 1).

In one embodiment, the average LCB particle size is between about 1 and about 10 cm in at least one dimension, such as between 4.5 and 5.5 cm, including any range or value therebetween, and the substrate is subjected to severe ammonia pretreatment conditions resulting in a downstream xylose yield more than two times higher than xylose yield of a similarly-sized substrate subjected to a low severity ammonia pretreatment. In a particular embodiment, xylose yield is increased from about 135 g/kg to about 165 g/kg (including any range or value therebetween) using LCB particles having an average particle size of about 5 cm in at least one dimension, severe ammonia pretreatment conditions and a GL of at least or about 6%.

In one embodiment, glucose yield is increased by at least 1% up to about 62%, including any range or value therebetween, or higher, depending on the particular LCB particle size or ratio of particle sizes (between 5 mm and about 5 cm, including any range or value therebetween, or higher), the pretreatment conditions and the GL. In one embodiment, glucose yield is increased by at least 60%, again, depending on the particular LCB particle size or ratio of LCB particle sizes (between 5 mm and about 5 cm, including any range or value therebetween, or higher), the pretreatment conditions and the GL. In a particular embodiment, glucose yield is increased from about 200 g/kg to about 325 g/kg, including any range or value therebetween, using LCB particles having an average particle size of about 5 cm in at least one dimension, severe ammonia pretreatment conditions and a GL of at least or about 6%.

In one embodiment, sugar yield is improved for a given size of larger LCB particles used herein (i.e., >5 mm) when using severe pretreatment conditions (e.g., high severity ammonia pretreatment conditions) as compared to low severity conditions, as these terms are defined herein. In one embodiment, sugar yield is improved for a given size of larger LCB particle used herein (i.e., >5 mm), when using severe pretreatment conditions (e.g., severe ammonia pretreatment conditions) as compared to low severity pretreatment conditions, as these terms are defined herein.

In one embodiment, sugar yield is increased for a 2 cm LCB particle by at least or about 30% with use of high severity versus low severity conditions. In one embodiment, sugar yield is increased for a 5 cm LCB particle by at least or about 50% with use of high severity versus low severity conditions. It is likely that larger-sized LCB particles, such as between about 1 and about 10 cm, including any range or value therebetween, or higher, can also result in comparable or even better yields as compared with conventional smaller-sized LCB particles, such as less than 5 mm.

In one embodiment, GL is between about 5% and about 6% such as between about 5.8% or about 6.2%, including any range therebetween. In one embodiment GL is at least or about 6%. In one embodiment, sugar yield is improved for a given size of larger LCB particle and a given pretreatment condition (i.e., low or high severity), depending on the GL. It is possible that higher GL's, such as between about 6% and about 9%, including any range or value therebetween, are also useful herein.

In one embodiment, recently harvested biomass or harvested biomass which has been stored for a period of time is size-adjusted into a LCB substrate containing particles with an average particle size of greater than or about 5 mm in at least one dimension. Any suitable size-adjusting device can be used, including, for example, choppers, blades, shears, etc. In one embodiment, the LCB is size-adjusted with a tub grinder set on a "chop" setting.

In one embodiment, the LCB is size-adjusted to have a particle size (or an average particle size) of greater than or about 5 mm in at least one dimension up to about 5 cm or higher in at least one dimension, including any range or value therebetween. In one embodiment, the resulting particle size is between about 0.5 cm in at least one dimension, up to about 10 cm, including any range or value therebetween. In one embodiment, the resulting particle size is between about 1 cm in at least one dimension, up to about 6 cm, including any range or value therebetween, such as, for example, between about 2 cm in at least one dimension, up to about 5 cm in at least one dimension. In one embodiment, the resulting particle size has a length of between about 0.5 cm up to about 5 cm or likely higher, such as up to 10 cm or higher, including any range or value therebetween, such as at least about 2 cm up to about 10 cm, such as between about 2 cm and about 5 cm, including any range or value therebetween.

It is understood that the LCB particles produced as a result of the size-adjusting step can have any suitable shape. In one embodiment, at least some, up to most, if not all of the LCB particles are substantially cylindrically shaped or rectangular shaped, with the stated dimension reflecting the larger dimension. In one embodiment, at least some up to most, if not all the LCB particles are substantially spherical in shape.

Any suitable LCB can be used, as the term is defined herein. In one embodiment, rice straw is used. In other embodiments, switchgrass, wheat straw and/or any other perennial or annual grasses can be used. It is also possible that the composition of the LCB can vary even if only one "type" of LCB is used, depending on whether some or all of the components of the plant are used, e.g., leaves, stems, flowers and/or seeds, etc.

The size-adjusted LCB substrate can be pretreated in any conventional manner known in the art. In one embodiment, the pretreatment process opens up the cell wall matrix of the LCB particle, hydrolyzes the hemicellulose, reduces cellulose crystallinity and ultimately makes the cellulose and hemicellulose more accessible to enzymes used in a subsequent hydrolysis process that converts the carbohydrate polymers into fermentable sugars. In one embodiment, liquid and/or gaseous ammonia pretreatment is used. In one embodiment, an ammonia fiber expansion (AFEX™) pretreatment, as defined, herein, is used. Such treatments can be performed according to the methods described in U.S. Pat. Nos. 6,106,888, 7,187,176, 5,037,663, and 4,600,590, each of which are hereby incorporated by reference in its entirety. Such treatments can include modified versions of such methods. For example, in one embodiment, rather than applying condensed or liquid ammonia to the biomass and allowing the ammonia and biomass to react as in conventional AFEX™ treatment, gaseous ammonia can be used. See, for example, U.S. Pat. No. 7,901,517, U.S. patent application Ser. Nos. 13/591,092, 12/976,344, and PCT Publication No. WO2012/088429, as well as various corresponding foreign patents and applications, each of which is hereby incorporated by reference herein in its entirety. By allowing ammonia gas, such as hot ammonia gas, to condense directly on cooler biomass, the ammonia and biomass become well-mixed. In various embodiments steam and/or water is also used during pretreatment.

In one embodiment, the downstream sugar yield is not only dependent on LCB particle size, but also on the pretreatment conditions. In one embodiment, the temperature, ammonia to biomass ratio, moisture content (dwb) and residence time of the pretreatment method for the LCB substrate are adjusted to maximize or enhance downstream sugar yield.

In one embodiment, high severity pretreatment conditions are used, as the term is defined herein. In one embodiment, the pretreatment conditions are comparable to the conditions referred to herein as AC2RS. In one embodiment, high severity pretreatment conditions result in a higher downstream sugar yield than low severity pretreatment conditions. In one embodiment, high severity pretreatment conditions are used with particles of a sufficient size (e.g., at least 10 cm) to alter the digestion pattern of the substrate as compared with low severity pretreatment conditions (which causes) faster hydrolysis, such that the substrate is essentially disintegrated after a given time period with only fine particles remaining in the hydrolysate. In contrast, in one embodiment, such larger-sized particles are subject to low severity pretreatment conditions which hydrolyze slowly, with the solids portion of the substrate remaining intact and causing only minor physical disintegration.

In one embodiment, the LCB is sized-adjusted and the pretreatment method is configured to enhance or maximize downstream sugar yield. For example, in one embodiment, the LCB is rice straw pretreated at a temperature of no less than about 140° C. In one embodiment, the temperature is between about 135 and 145° C., including any range or value therebetween. In one embodiment the temperature is between about 80 and about 180° C., such as between about 80 and about 160° C., such as between about 100 and about 140° C., such as between about 120 and about 130° C., including any ranges and values therebetween.

In one embodiment, the ammonia to biomass ratio is between about 0.5:1 and about 3:1, such as between about 1:1 and about 2:1, including any range or value therebetween, although it is possible that ammonia to biomass ratios up to about 4:1 may be useful herein. In one embodiment, the ammonia to biomass ratio is no more than 1:1. In one embodiment, the ammonia to biomass ratio is no less than or about 1:1.

In one embodiment, the biomass inherently has or is adjusted to have between about 10 and about 150% moisture content (dwb), such as between about 100 and about 130% (dwb), or between about 125 and about 135% (dwb), including any range or value therebetween. In one embodiment, the biomass is no less than or about 130% (dwb).

In one embodiment, the residence time for pretreatment is on the order of seconds or minutes up to about one or more hours, such as between about 15 and about 80 minutes or between about 30 and about 60 minutes, including any range or value therebetween. In one embodiment, the residence time is at least or about 50 minutes.

In one embodiment, the biomass is an AFEX™ treated biomass substrate which is pretreated under conditions that are greater than the glass transition temperature, i.e., "severe" pretreatment conditions. In one embodiment, the temperature of the substrate is increased to at least or to about 140° C., the ammonia to biomass ratio is no less than or about 1:1, the moisture content (dwb) is no less than or about 130% moisture and the residence time is no less than or about 50 minutes. In a particular embodiment, the conditions include a temperature of approximately 140° C.; an ammonia to biomass (e.g., rice straw, switchgrass, corn stover, etc.) ratio of approximately 1:1 ammonia to biomass ratio, a moisture content (dwb) of approximately 130% moisture and a residence time of approximately 50 minutes ("C2" conditions as described in the example).

The various embodiments will be further described by reference to the following examples, which are offered to further illustrate various embodiments of the present invention. It should be understood, however, that many variations and modifications may be made while remaining within the scope of the various embodiments.

Example 1

The effect of two optimized AFEX™ pretreatment conditions on different particle sizes of rice straw was determined, followed by low and high solid loading enzymatic hydrolysis, and a determination of the estimated sugar yield. Enzymatic hydrolysis data for each particle size was also fitted into the Chrastil kinetic model to determine kinetic parameters. SEM imaging was performed to explain the effect of AFEX™ pretreatment conditions on the hydrolysis kinetics at different particle sizes.

Chastril Model

The complexity of the enzymatic hydrolysis of LCB stems from the fact that it is a heterogeneous insoluble substrate, and thus, enzymatic hydrolysis is limited by access to available surfaces. In such a heterogeneous system, it is possible to study enzymatic hydrolysis kinetics using time course data. Also, it is possible that these enzymatic reactions are diffusion limited, and therefore, the hydrolysis time curves depend strongly on the heterogeneous rate-limiting structures of the substrate-enzyme system. The following equation shows the diffusion-limited kinetic model proposed by Chrastil (See Chrastil J: Enzymatic product formation curves with the normal or diffusion limited reaction mechanism and in the presence of substrate receptors. *Int J Biochem* 1988, 20(7): 683-693, which is hereby incorporated by reference in its entirety).

In this model, two factors determine the system behavior, i.e., initial enzyme concentration and the equilibrium product concentration:

$$P = P_e(1 - e^{-kE_o t})^n$$

wherein P is the product concentration at time T and $P_e$ is the equilibrium product concentrations; k is a rate constant proportional to the diffusion coefficient as defined by Fick's law, $E_o$ the initial enzyme concentration and n is a structural diffusion resistance constant depending on the steric features of the system. The parameter n defines the reaction order characteristics. When diffusion resistance is small, n tends to 1 (for low-resistance films n=0.9-1) and the reaction is of apparent first order. If the system is strongly limited by diffusion resistance, n is small (high-resistance structures n=0.5-0.6). In addition, when n>1, a consecutive reaction order may be expected.

Starting Materials

Rice straw from a medium-grain rice crop obtained from a field in the central part of Selangor, Malaysia harvested October 2009 and rice straw from California were harvested February 2008 and used in this testing. The harvested biomass was air-dried to <10% moisture content (dwb). Some of the rice straw was milled using a Foss mill (Eden Prairie, Minn.) and passed through 2 mm and 5 mm screens, while other samples were cut by hand using scissors to dimensions of either about 2 cm or about 5 cm. All processed rice straw samples were labelled as 2 mm, 5 mm, 2 cm and 5 cm and were stored in a refrigerator (4° C.) until used. Each sample of rice straw tested contained a collection of particles referred to herein as a "substrate."

AFEX™ Pretreatment

The logarithm of the reaction ordinate (log Ro) is defined as the severity of the pretreatment, wherein the reaction ordinate is as follows:

$$R_o = t \times e^{\left[\frac{(T_r - T_b)}{14.75}\right]}$$

Wherein "t" is the residence time (min), "Tr" is the treatment temperature (° C.), "$T_b$" is the base temperature (100° C.) and "14.75" is the activation energy.

Two statistically optimized AFEX™ pretreatment conditions identified as C1 (100° C.; 2:1 ammonia to biomass ratio (w:w); 80% moisture (dwb), 30 minutes residence time and severity, log $R_o$=1.48) and C2 (140° C.; 1:1 ammonia to biomass ratio (w:w); 130% moisture (dwb), 50 minutes residence time and severity, log $R_o$=2.88) were used to pretreat the rice straw.

Initially, deionized water was added to the rice straw to increase the moisture content to the desired level. Rice straw at the predetermined moisture level was then loaded into a bench top high-pressure Parr reactor having a capacity of 2000 mL (PARR Instrument Co., Illinois). The desired amount of liquid ammonia purchased from Airgas, Inc. was then loaded to the reactor using high pressure stainless steel canister. The reactor temperature (and consequently the temperature of the biomass contained therein, i.e., the reaction temperature) was raised and maintained at the desired temperature for either 30 or 50 minutes and under 400 psi pressures as outlined in Balan V, et. al., *Mushroom spent straw: a potential substrate for an ethanol-based refinery*. J Ind Microbiol Biotechnol 2008, 35: 293-301, which is hereby incorporated by reference herein in its entirety.

Under these conditions, the ammonia diffused into the biomass and caused the biomass to swell. AFEX™ C1 treated rice straw (i.e., AC1RS) substrates of different particle sizes were labelled as: AC1RS-2 mm, AC1RS-5 mm, AC1RS-2 cm, AC1RS-5 cm, while AFEX™ C2 treated rice straw (i.e., AC2RS) substrates were labelled as: AC2RS-2 mm, AC2RS-5 mm, AC2RS-2 cm and AC2RS-5 cm. All samples of AC1RS and AC2RS substrates were allowed to dry under the fume hood overnight to remove residual ammonia. The samples were then placed in re-sealable plastic bags and stored in a freezer (–20° C.) until used.

Composition Analysis

Composition analysis was performed on untreated rice straw (URS) substrates and AFEX™ treated rice straw (AC1RS and AC2RS) substrates using milled rice straw of 5 mm particle size) according to Laboratory Analysis Protocol (LAP) developed by the National Renewable Energy Laboratory, Golden, Colo. USA (See Hames B, Scarlata C, Sluiter A: *Determination of protein content in biomass*. NREL Laboratory Analytical Procedures. National Renewable Energy Laboratory, Golden, Colo., USA; 2008, which is incorporated hereby by reference in its entirety. (Hereinafter "NREL 2008").

Water and ethanol (95%) extraction were carried out using an ASE2000 Accelerated Solvent Extractor from Dionex (Sunnyvale, Calif.) to remove the extractives before quantifying the structural carbohydrates and lignin in the acid hydrolysis step. Both the un-extracted and extractives-free materials were used for comparison purposes in subsequent analyses. Crude protein content was calculated based on nitrogen content in the biomass determined using a Skalar Primacs$^{SNC}$ Total Nitrogen Analyzer (Breda, Netherlands), which relies on combusting all nitrogen to NOx and quantify them.

Enzymatic Hydrolysis

Enzymatic hydrolysis of URS and AFEX™ treated rice straw substrates was performed according to the Laboratory Analysis Protocol (LAP 009) developed by National Renewable Energy Laboratory (NREL 2008). The hydrolysis was carried out at low (1%) and high (3%) GL (w/v) in a 15 mL reaction volume using 20 mL scintillation vials and 50 mL BD Falcon™ tubes, respectively. Higher GL (6%, (w/v) equivalent to 17% of solid loading on dry weight basis) was conducted in a 300 mL reaction volume using a 2000 mL Erlenmeyer flask.

The enzyme mixture comprised Spezyme® CP (Batch no: 4900901224) from Genencor International (Rochester, N.Y.), and Novozyme™ 188 (Batch no: 078K0709) from Sigma-Aldrich Co. (St. Louis, Mo.). The hydrolysis samples of 1%, 3% and 6% GL were mixed with the desired cellulase enzymes at 15 FPU/g glucan (protein concentration 123 mg/ml) and a β-glucosidase enzyme loading of 64 pNPGU/g glucan (protein concentration of 168 mg/ml).

The hydrolysis reaction for 1% and 3% GL was carried out at 50° C., 150 rpm, and a pH of 4.8 using 1M citrate buffer (pH 4.8) using citric acid and NaOH purchased from Sigma-Aldrich. Antibiotics (Tetracycline (40 mg/L) and cycloheximide (30 mg/L)) from Sigma-Aldrich were added in the hydrolysis samples to avoid microbial contamination. For 6% GL, the hydrolysis reaction was buffered same as above and carried out at the same temperature and pH with a shaker speed of 250 rpm to achieve good mixing performance. High solid loading hydrolysis (6% GL) was done using the method of Lau M W, Dale B E: Cellulosic ethanol production from AFEX-treated corn stover using *Saccharomyces cerevisiae* 424A(LNH-ST). Proc Natl Acad Sci USA 2009, 106:1368-1373, which is hereby incorporated herein by reference in its entirety. (Hereinafter "Lau and Dale 2009").

Hydrolysate samples for the 1% and 3% GL experiments were taken at specified time intervals (4 hr, 8 hr, 12 hr, 24 hr, 48 hr, 72 hr and 168 hr) and placed in capped microcentrifuge tubes, heat-treated at 100° C. for 20 minutes on a heating block (to denature the enzyme), centrifuged at 4400 rpm for 10 minutes and then filtered through a 0.22-μm Whatman® membrane syringe filter. After 168 hr, the hydrolysate for the 6% GL experiment was centrifuged at 6000 rpm and then at 10,000 rpm to separate the hydrolysate from un-hydrolysed solids (Lau and Dale 2009).

HPLC Analysis for Monomeric Sugars

The monomeric sugars (i.e., glucose, xylose and arabinose) were analyzed using high performance liquid chromatography (HPLC). The HPLC system comprised a Shimadzu LC-2010 water pump (Milford, Mass.) equipped with a Waters 410 refractive index detector. An Aminex HPX-87P column (Bio-Rad, Sunnyvale, Calif.) equipped with a de-ashing guard cartridge (Bio-Rad) was used for monomeric sugars concentration analysis in hydrolysate. Degassed HPLC grade water was used as the mobile phase at 0.6 ml/min at a column temperature of 85° C. The Aminex HPX-87H column was then used to quantify the sugars concentrations in the acid hydrolysis samples for compositional and oligomers analysis. Five (5) mM sulfuric acid ($H_2SO_4$) General Chemicals was used as the mobile phase at 0.6 ml/min at a column temperature of 50° C. The HPLC sample injection volume was 10 μl with a run time of 20 min. Standard curves were generated using different concentrations of mixed sugars (Balan et al. 2008).

Sugar Conversion and Yield

AFEX™ pretreatment is a dry to dry process, and therefore the sugar recovery in the rice straw after AC1RS and AC2RS treatments depended primarily on the pretreated solid recovered after the pretreatment. The sugar conversion after enzymatic hydrolysis was calculated using the actual sugar produced in the hydrolysis over the available theoretical sugar in the rice straw, while the sugar yield was calculated using the actual mass of total sugar produced over the actual mass of URS (dwb) used in the hydrolysis. Below are the equations used in the calculations:

$$\text{Overall sugar conversion (\%)} = \frac{(C_{Mono} + C_{Oligo}) \times V}{TSC}$$

$$\text{Overall sugar yield (\%)} = \frac{(C_{Mono} + C_{Oligo}) \times V}{W_{URS}}$$

wherein $C_{Mono}$ and $C_{Oligo}$ are the monomeric and oligomeric sugar concentrations in g/L, V is the volume of enzymatic hydrolysis reaction in L, TSC is the theoretical sugar content in the hydrolysis at specified GL in g, and $W_{URS}$ is the weight of the URS in kg (dwb).

Kinetic Modelling and Parameter Estimation

The experimental data on enzymatic hydrolysis of URS (5 mm and 5 cm), AC (2 mm, 5 mm, 2 cm and 5 cm) and AC2RS (2 mm, 5 mm, 2 cm and 5 cm) substrates at 1% and 3% GL were fitted according to the equation: $P=P_e(1-e^{-kE_o t})^n$. The parameters, "k" and "n" of the model were determined using the Generalized Reduced Gradient (GRG) Nonlinear algorithm in Microsoft® Excel® Solver.

Scanning Electron Microscopy (SEM) Imaging of URS and AFEX™—Pretreated Rice Straw Composition Scanning electron microscopy (SEM: ZEISS-EVO MA 10, UK, EDX: EDAX-APOLLO X, USA) studies were conducted to examine the histological changes on the exterior and interior epidermis of rice straw after AFEX™ pretreatment. All samples were coated with a thin layer of gold using a DC sputter coater (QUORUM Q150RS, UK). The samples were mounted carefully on the SEM stub and gently pressed for few seconds.

Composition Analysis of URS and AFEX™ Treated Rice Straw

Table 1 shows composition of URS, AC1RS and AC2RS substrates. For structural carbohydrates (glucan, xylan, arabinan, and acetyl) and lignin, the values in Table 1 are based on an extractive-free sample, which are then corrected by the identified extractives in the reported extractives, including soluble sugars and soluble oligo sugars. However, since xylan and arabinan contain primarily soluble oligo sugars anyway, such values are identical to the values reported in U.S. Patent Application Ser. No. 61/606,139 ('139) which did not include soluble sugars. The lignin values in Table 1 differ from the values reported in U.S. Patent Application Ser. No. 61/606,139 ('139) because the new value excludes the insoluble native protein from biomass. In contrast to glucan, the "extractives" values in Table 1 exclude the identified extractives, i.e., soluble sugars, soluble oligo sugars and soluble protein since these values are already reported in their correct constituents, i.e., glucan. AC2RS substrates also retained higher nitrogen amounts as compared to AC1RS substrates, namely 3.7% versus 2.5% nitrogen content (Table 1). There is no dramatic change in ash content after pretreatment.

TABLE 1

Composition of URS, AC1RS and AC2RS Substrates

| Composition | URS - Malaysia | URS - USA[a] | AC1RS - Malaysia | AC2RS - Malaysia |
|---|---|---|---|---|
| Glucan | 34.4 ± 0.6[1] | 34.7 | 33.8 ± 0.2[5] | 34.6 ± 0.4[8] |
| Xylan | 19.7 ± 0.2 | 15.1 | 19.8 ± 0.2 | 19.5 ± 0.1 |
| Arabinan | 3.7 ± 0.1[2] | 2.2 | 3.6 ± 0.0 | 3.7 ± 0.1 |
| Lignin | 19.8 ± 0.8[3] | 19.1 | 15.4 ± 0.8[6] | 15.8 ± 1.0[9] |
| Acetyl | 1.6 ± 0.1 | NA | 1.4 ± 0.1 | 1.7 ± 0.0 |
| Nitrogen in biomass | 0.5 ± 0.2 | NA | 0.5 ± 0.2 | 0.5 ± 0.2 |
| Nitrogen from AFEX™ | 0 | NA | 2.5 ± 0.4 | 3.7 ± 0.4 |
| Ash | 14.1 ± 0.2 | 16 | 13.5 ± 0.1 | 13.4 ± 0.2[10] |
| Extractives | 6.7 ± 1.8[4] | 17.9 | 11.8 ± 1.4[7] | 12.8 ± 1.0[11] |

[a]Zhong et al. Optimization of enzymatic hydrolysis and ethanol fermentation from AFEX™-treated rice straw. Appl Microbiol Biotechnol 2009, 84(4): 667-676.
NA = Not available
[1]previously reported in '139 as 33.5 based on extractive-free sample only
[2]previously reported in '139 as 3.8 based on extractive-free sample only
[3]previously reported in '139 as 21.0 which includes insoluble native protein
[4]previously reported in '139 as 10.4 which includes some identified constituents in the extractives
[5]previously reported in '139 as 32.6 based on extractive-free sample only
[6]previously reported in '139 as 16.6 which includes insoluble native protein
[7]previously reported in '139 as 17.9 which includes some identified constituents in the extractive
[8]previously reported in '139 as 32.9 based on extractive-free sample only
[9]previously reported in '139 as 16.9 which includes insoluble native protein
[10,11]corrected from values previously reported in '139

The structural carbohydrates of AC1RS and AC2RS substrates were 57.2% and 57.8%, respectively, and were comprised of about 33.8 to about 34.6% glucan, about 19.5 to about 19.8% xylan, and about 3.6 to about 3.7% arabinan. A statistical paired t-test on the mean composition of URS, AC1RS and AC2RS substrates indicated that the differences in compositions of the carbohydrate components (i.e., glucan, xylan and arabinan), acetyl groups, and ash, were statistically insignificant (t-stat<$t_{critical}$ and p>0.05). This result was likely due to the "dry to dry" nature of the AFEX™ process, which prevents the loss of holocellulosic components during pretreatment of rice straw.

The compositions of lignin, nitrogen and extractives between URS, ACR1S and ACR2S substrates showed significant differences (t-stat>$t_{critical}$ and p<0.05). The decrease in lignin in both AC1RS and AC2RS substrates was potentially due to the lignin degradation during the AFEX™ pretreatment, which caused the lignin to solubilize and re-deposit on the surface of the rice straw. During the two-stage acid hydrolysis step of compositional analysis, the newly re-deposited lignin was released in the form of acid soluble lignin, as indicated by an increase in the amount of total extractives. The increase in nitrogen levels in both AC1RS and AC2RS was mainly due to the chemical reaction between ammonia and biomass during the AFEX™ pretreatment itself.

These results are surprising, as the ratio of ammonia to solid for the AC1RS substrates (1:1) was one-half the ratio of the AC2RS substrates (2:1). This may indicate that with the higher reaction temperature (140° C.) of AC2RS, more ammonia was able to penetrate the cellulose resulting in formation of ammonia-cellulose complexes. This formation likely led to the incorporation of ammonia into the cellulose crystal lattice, causing lattice transformation and crystal plane widening, known as a "swelling effect." Most of the ester linkages were likely broken during this process resulting in solubilization of lignin residues and re-deposition on the surface when ammonia was removed from the reactor.

During AFEX™ pretreatment, ammonia incorporated into the biomass has the tendency to cleave the ester linkages of AGX via ammonolysis and hydrolysis reactions. In this testing, the increase in the total extractives of AC1RS and AC2RS substrates after water and ethanol extractions indicated that AFEX™ pretreatment chemically cleaved the structure of lignin and AGX in LCCs. The cleaved hemicelluloses and lignin residues were then easily extracted and solubilized. The total extractives extracted from the rice straw, including the water soluble products, acid soluble lignin, soluble proteins, soluble salts and minerals, and other minor components, significantly increased as the severity of the pretreatment increased, with the AC1RS substrate containing 25.3% extractives and AC2RS treated rice straw containing 30.2% soluble extractives (URS: 14%).

FIG. 1 characterizes the composition of the total extractive content in the substrates based on extractives in water and ethanol extractions. FIG. 1 is in contrast to FIG. 2 in the '139 Application, which did not include the extractable native protein (originally present in biomass) and extractable nitrogen from AFEX™ pretreatment. FIG. 2 in the '139 Application further included certain computational errors which resulted in improperly indicating that AC2RS had fewer extractives than AC1RS. Corrected values are now shown in FIG. 1. Cleavage of LCC was supported by an increase in soluble oligomeric sugars (i.e., xylose and arabinose) found in the water extracts of both the AC1RS and AC2RS substrates. In comparison to water extraction of URS (FIG. 2), water extraction of AC1RS and AC2RS substrates yielded a 4.1- and 6.2-fold increase, respectively, of soluble xylose oligomers and a 4.1- and 7.3-fold increase, respectively, of soluble arabinose oligomers.

The water extraction of AC1RS and AC2RS substrates resulted in a 16- and 19-fold increase, respectively, of soluble acetyl in comparison with the soluble acetyl produced in the water extraction of the URS (FIG. 1). This increase in soluble acetyl is likely due to the dissolution of O-acetyl group on the xylan-pyranose backbone side chain via ester bond cleavage during AFEX™ pretreatment.

Xylan in the cell wall of graminaceous plants, such as rice straw, is composed of approximately 1 to 2% of O-acetyl group. Hemicellulose components (xylose, arabinose and acetyl) dissolved and solubilized more during water extraction of AC2RS substrates as compared with AC1RS substrates, indicating an increased occurrence of structural disruptions (i.e., disruptions of the LCC linkages) under the more severe AC2RS conditions.

As such, it appears that pretreatment factors such as temperature, residence time, alkali/acid concentration, and/or moisture content, can influence the release of hemicelluloses and lignin degradation products.

Other unquantified extractable materials (classified as other extractives), may include gums, resins, pitch, waxes, sterols, flavinoids, tannins, terpenes, quinones, non-structural sugars, chlorophyll and other minor building blocks. It was observed that the fraction of other extractives (non-quantified components) was higher in both of the AC1RS and AC2RS substrate extractives as compared to URS, 6.6% (FIG. 1).

Figure 2A:
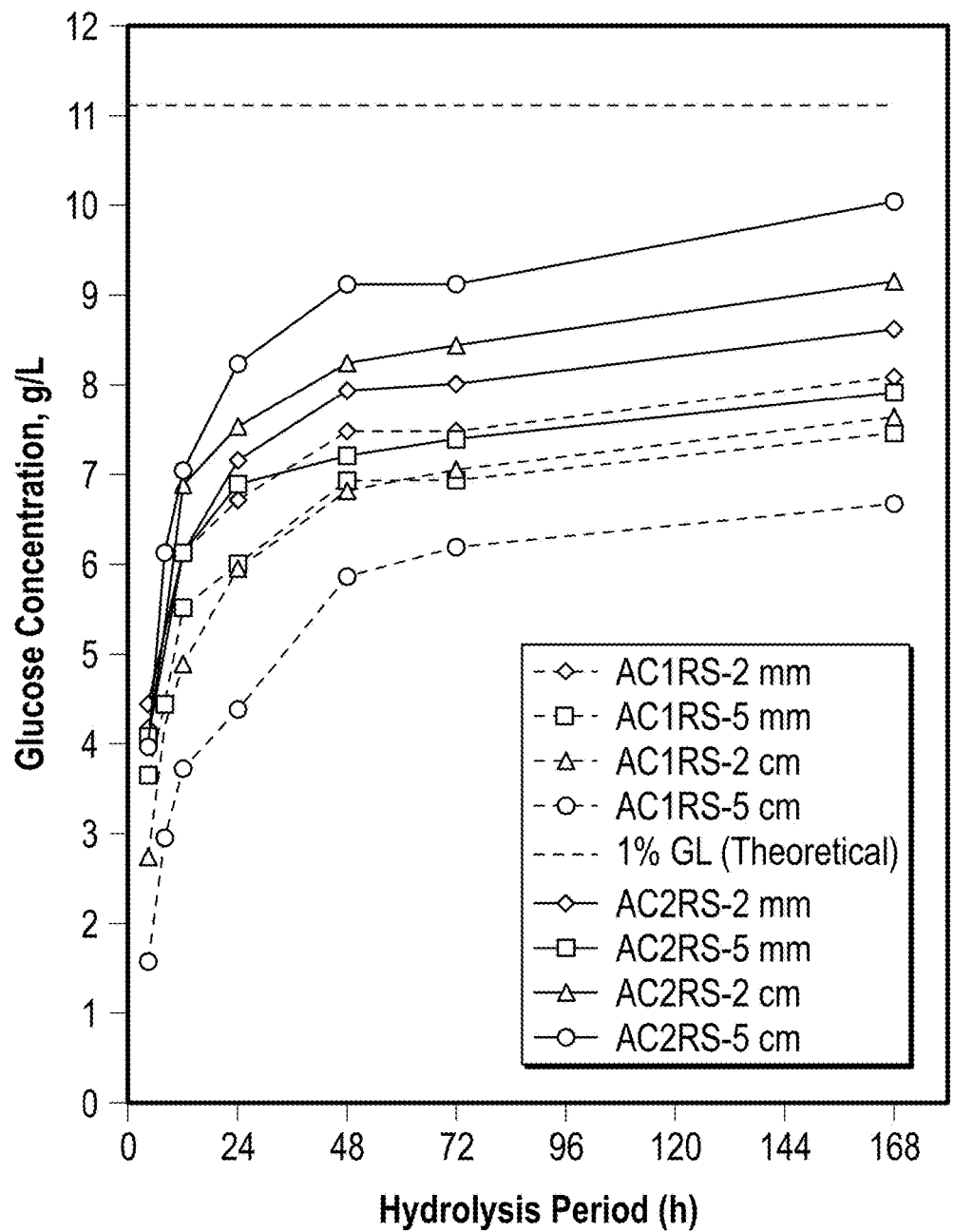
FIGS. 2A and 2B are graphs showing monomeric sugar concentrations profiles for glucose (2A) and xylose (2B) at 1% GL under C1 and C2 conditions for different hydrolysis periods and particle sizes according to various embodiments.
Figure 2B:
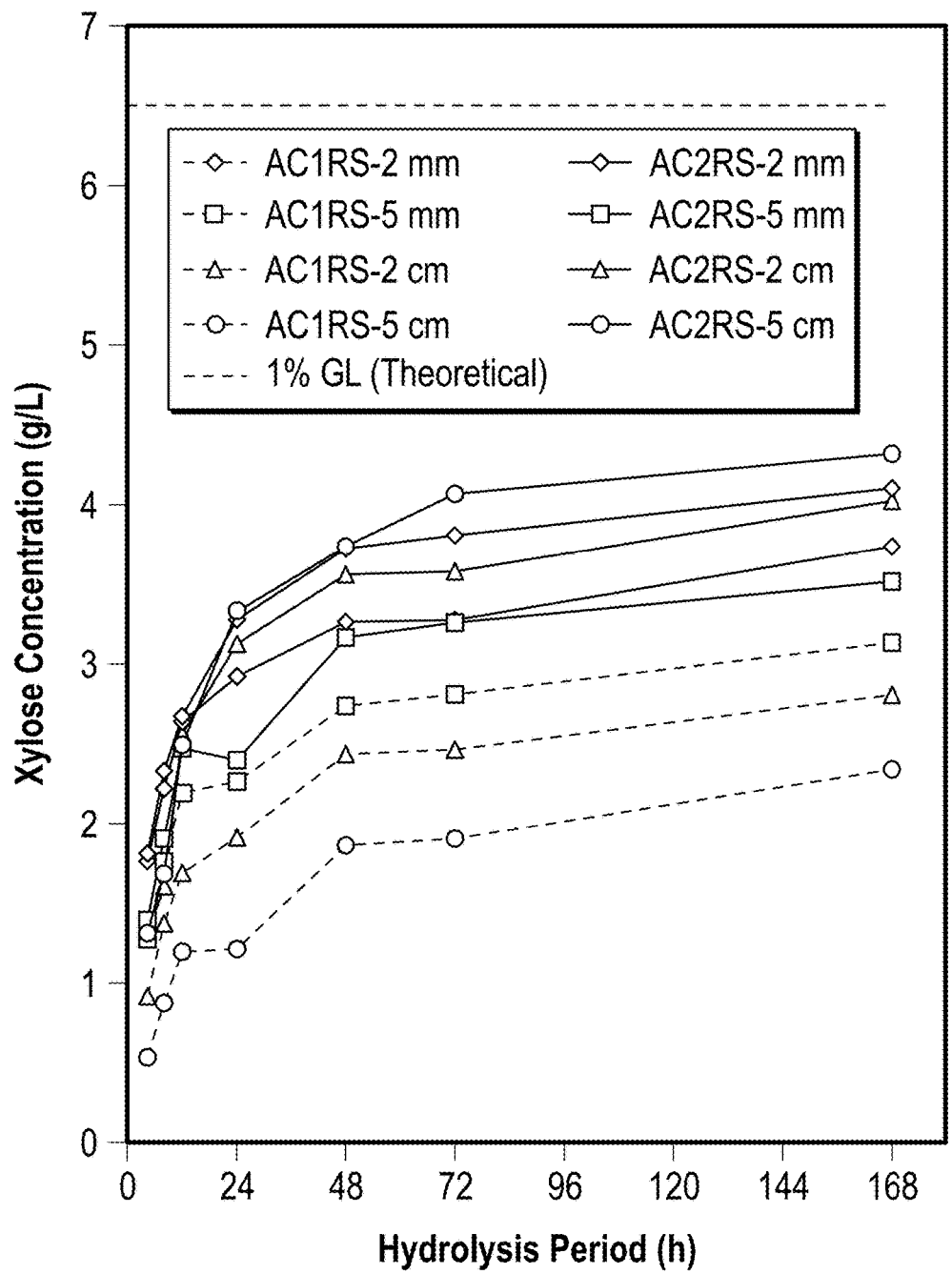

Enzymatic Hydrolysis and Kinetic Modelling of AC1RS and AC2RS Substrates Low Solid Loading Hydrolysis (1% GL)—Monomeric Sugar Release FIGS. 2A-2B are graphs showing monomeric sugar concentration profiles for glucose (FIG. 2A) and xylose (FIG. 2B) at 1% GL for AC1RS and AC2RS substrates for different hydrolysis periods, namely 4 hr, 8 hr, 12 hr, 24 hr, 48 hr, 72 hr and 168 hr, and biomass sizes, namely 2 mm, 5 mm, 2 cm and 5 cm using 15 mL, Novozyme™ and Spezyme® CP, 50° C. and 150 rpm. Maximum theoretical sugar concentrations are indicated by the dashed line at the top of each figure.

As can be seen in FIGS. 2A and 2B, glucose and xylose were rapidly released at the beginning of the enzyme hydrolysis process. Thereafter, the sugar generation rate slowed down as hydrolysis proceeded. At the 1% GL, about 50 to about 80% of the total glucose and xylose released were liberated within the first 12 hr of hydrolysis. The simplified model of enzymatic hydrolysis divided the hydrolysis into two stages, i.e., the initial stage, where the rate was almost linear, and the final stage, where the rate continuously decreased.

Figure 6A:
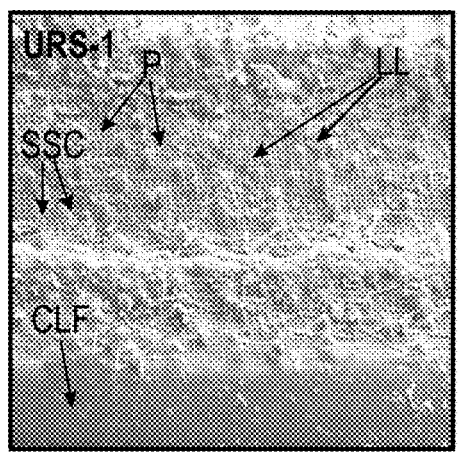
FIGS. 6A-6I are SEM images of 5 cm LCB untreated and treated particles at various magnifications: URS (FIGS. 6A-6C), AC1RS (FIGS. 6D-6F), and AC2RS (FIGS. 6G-6I) according to various embodiments.
Figure 6B:
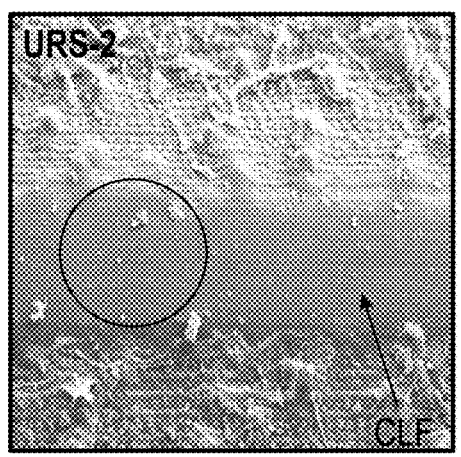
Figure 6C:
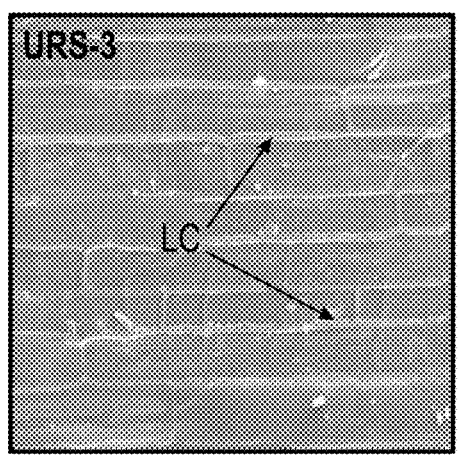
Figure 6D:
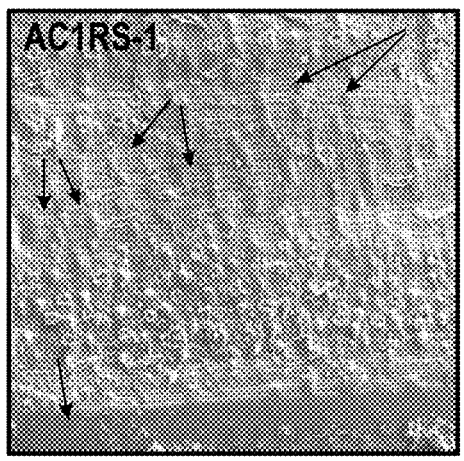
Figure 6E:
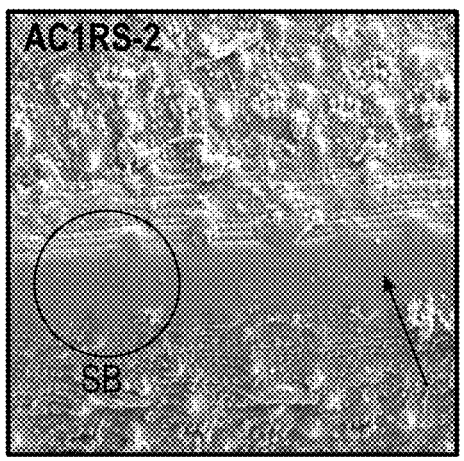
Figure 6F:
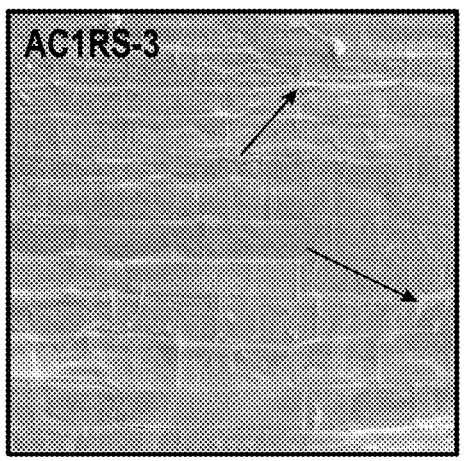
Figure 6G:
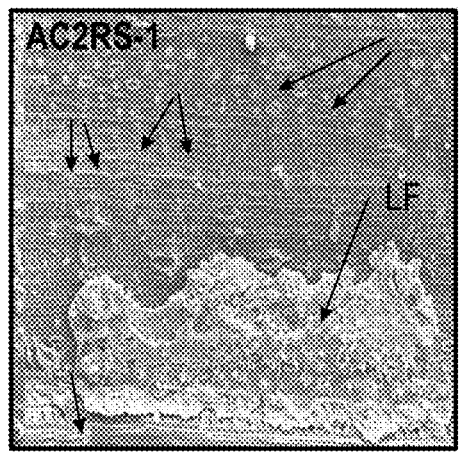
Figure 6H:
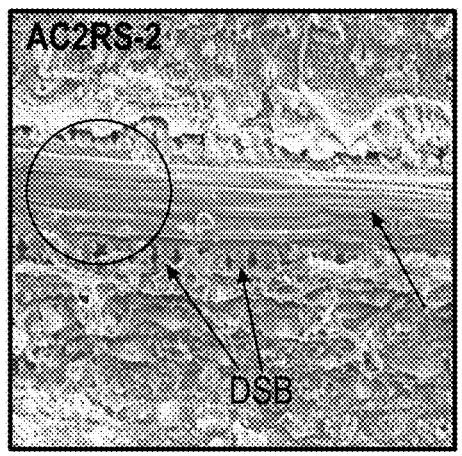
Figure 6I:
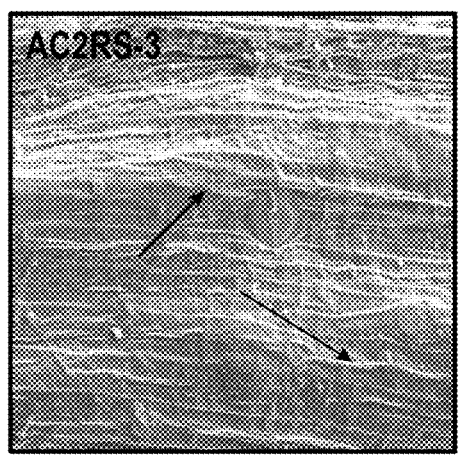

As shown in Table 2 and FIG. 2A, at 1% GL hydrolysis, AC1RS substrates hydrolyzed at a low initial hydrolysis rate during the first 12 h (linear slope), and the rates ranged from 0.31 g/L·h (AC1RS-5 cm) to 0.51 g/L·h (AC1RS-2 mm) This slow hydrolysis of AC1RS substrates produced low glucose and xylose concentrations at the end of 168 h hydrolysis (FIGS. 6G-6I). Among AC1RS substrates, only the smaller-sized rice straw of AC1RS-2 mm produced the highest final glucose concentration with 8.1 g/L. The smaller sizes of rice straw of AC1RS-5 mm and AC1RS-2 cm had approximately similar glucose concentrations: 7.5 g/L and 7.6 g/L, respectively. The substrates comprised of the largest particles sizes of AC1RS, AC1RS-5 cm, had the lowest glucose concentration of 6.7 g/L. A similar decreasing trend was also observed for the xylose concentration for all AC1RS substrates.

In contrast and as shown in Table 2, a different trend of sugar production was observed in the hydrolysis of most AC2RS substrates (at 1% GL) (FIGS. 2A and 2B). These AC2RS substrates quickly hydrolyzed during the first 12 h with the initial hydrolysis rate ranging from 0.51 g/L·h (AC2RS2 mm and AC2RS-5 mm) to 0.59 g/L·h (AC2RS-5 cm). The fast hydrolysis of AC2RS substrates produced higher glucose and xylose concentrations at the end of 168 h hydrolysis when compared to AC1RS substrates (except for AC2RS-5 mm where the concentration slightly dropped after 24 h).

After 4 hr of hydrolysis, glucose and xylose concentrations in the particles pretreated according to the more severe AC2RS conditions, i.e., AC2RS hydrolysates (solid lines) were higher than in AC1RS hydrolysates (dotted lines). A dominant factor affecting the reaction rate at the beginning of 1% GL hydrolysis appears to be the severity of the chemical pretreatment conditions.

Of particular interest and as shown in FIGS. 4A-4D, the larger-sized rice straw (5 cm) demonstrated different digestion patterns during enzymatic hydrolysis when treated under the milder AC1RS conditions as compared to the more severe AC2RS conditions.

AC2RS-5 cm had the highest glucose production of 10 g/L, while AC2RS-2 cm had a slightly lower concentration of 9.2 g/L. However, AC2RS milled rice straw (AC2RS-2 mm and AC2RS-5 mm) had lower glucose concentrations of 8.6 g/L and 7.9 g/L, respectively. AC2RS-5 cm also produced the highest xylose concentration with 4.3 g/L, almost a two-fold increase, when compared to AC1RS-5 cm, while AC2RS-2 cm had a glucose production of 4 g/L, as compared with the 2.8 g/L for AC1RS-2 cm at 1% GL. Both 2 mm and 5 mm milled rice straw did not show significant difference in xylose concentrations when pretreated using either the AFEX™ C1 or C2 condition (Table 2).

Such results are surprising, as they are contrary to the generally accepted understanding that particles an order of magnitude smaller provide the best downstream sugar yield.

Figure 3A:
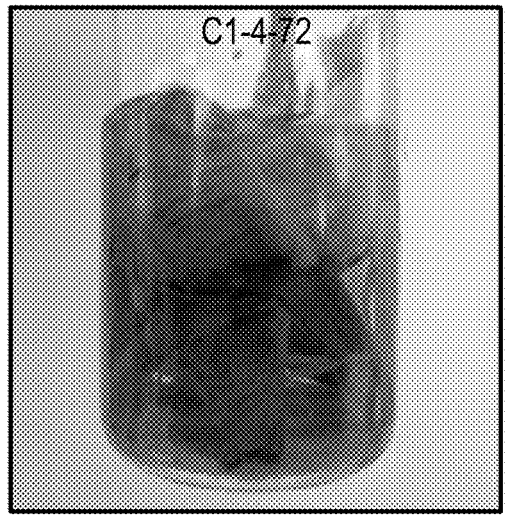
FIGS. 3A-3D are images of rice straw (5 cm) pretreated under C1 conditions (FIGS. 3A and 3C) and C2 conditions (FIGS. 3B and 3D) after undergoing enzymatic hydrolysis at 1% GL, with FIGS. 3A and 3B showing AC1RS and AC2RS, respectively, after 72 hr of hydrolysis and FIGS. 3C and 3D showing AC1RS and AC2RS, respectively, after 168 hr of hydrolysis according to various embodiments.
Figure 3B:
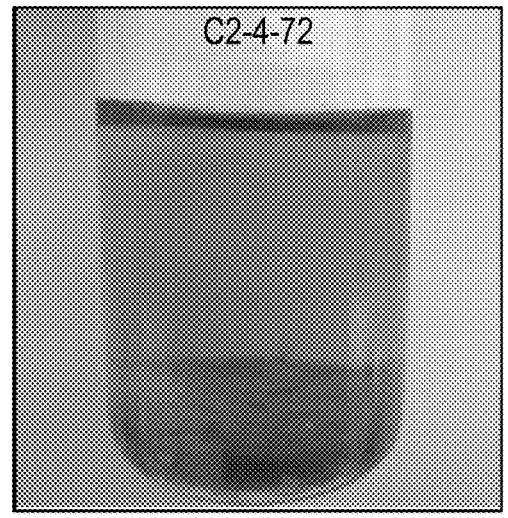

FIGS. 3A and 3B show the glucan (3A) and xylan (3B) conversion at 1% GL hydrolysis at the 4 h and 168 h hydrolysis period. In both figures, AC1RS substrates showed a declining sugar conversion trend as the size of the particles in the substrates increased (i.e., small: AC1RS-2 mm>AC1RS-5 mm, large: AC1RS-2 cm>AC1RS-5 cm). After 168 h hydrolysis of AC1RS substrates, AC1RS-2 mm produced the highest glucan and xylan conversions with 72.8% and 57.5%, respectively, while AC1RS-5 cm gave the lowest glucan and xylan conversions at only 60.2% and 36.1%, respectively.

Figure 4A:
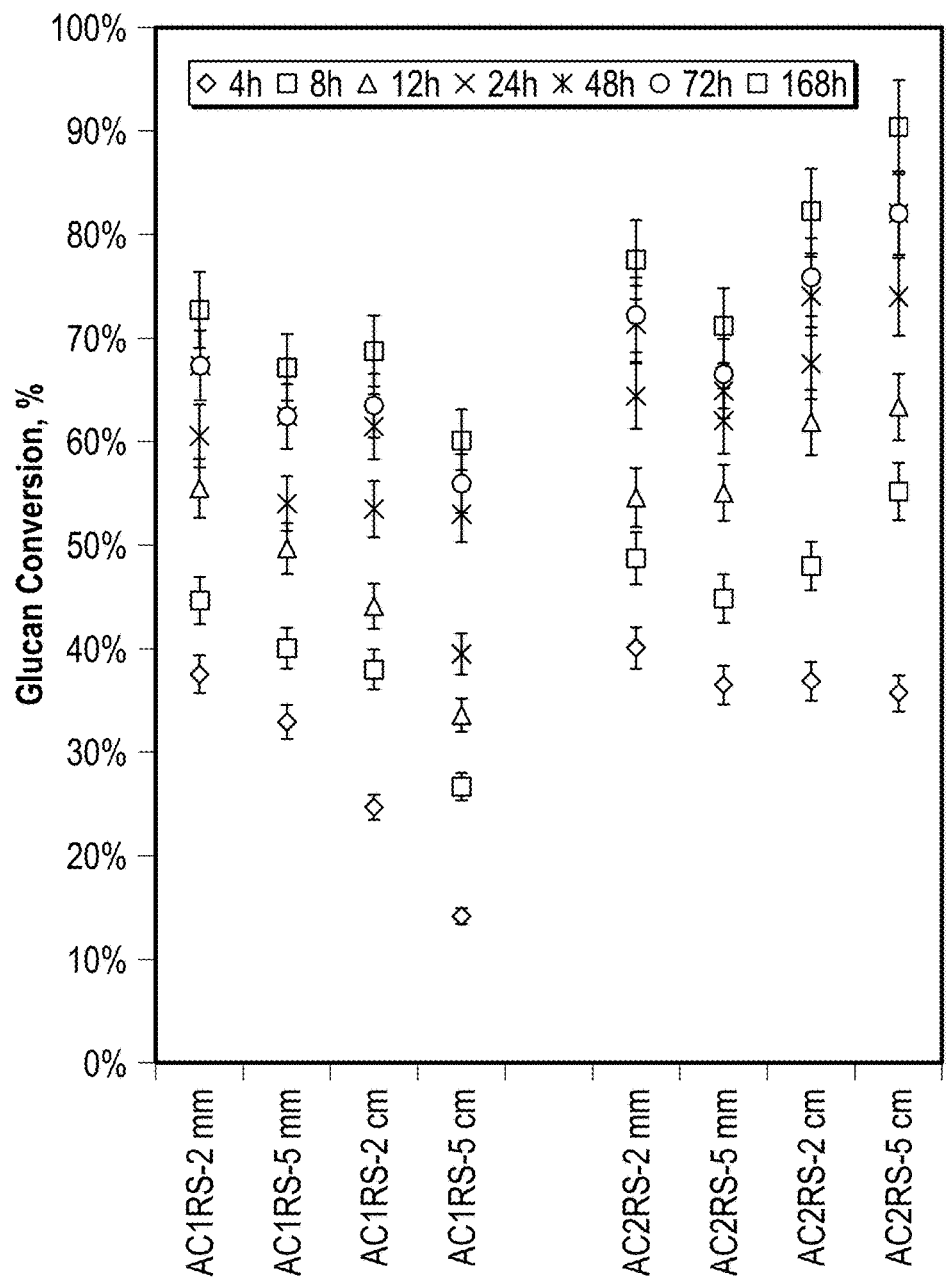
FIGS. 4A and 4B are graphs showing glucan (FIG. 4A) and xylan (FIG. 4B) conversion profiles at 1% GL under C1 and C2 conditions for different hydrolysis periods and particle sizes according to various embodiments.
Figure 4B:
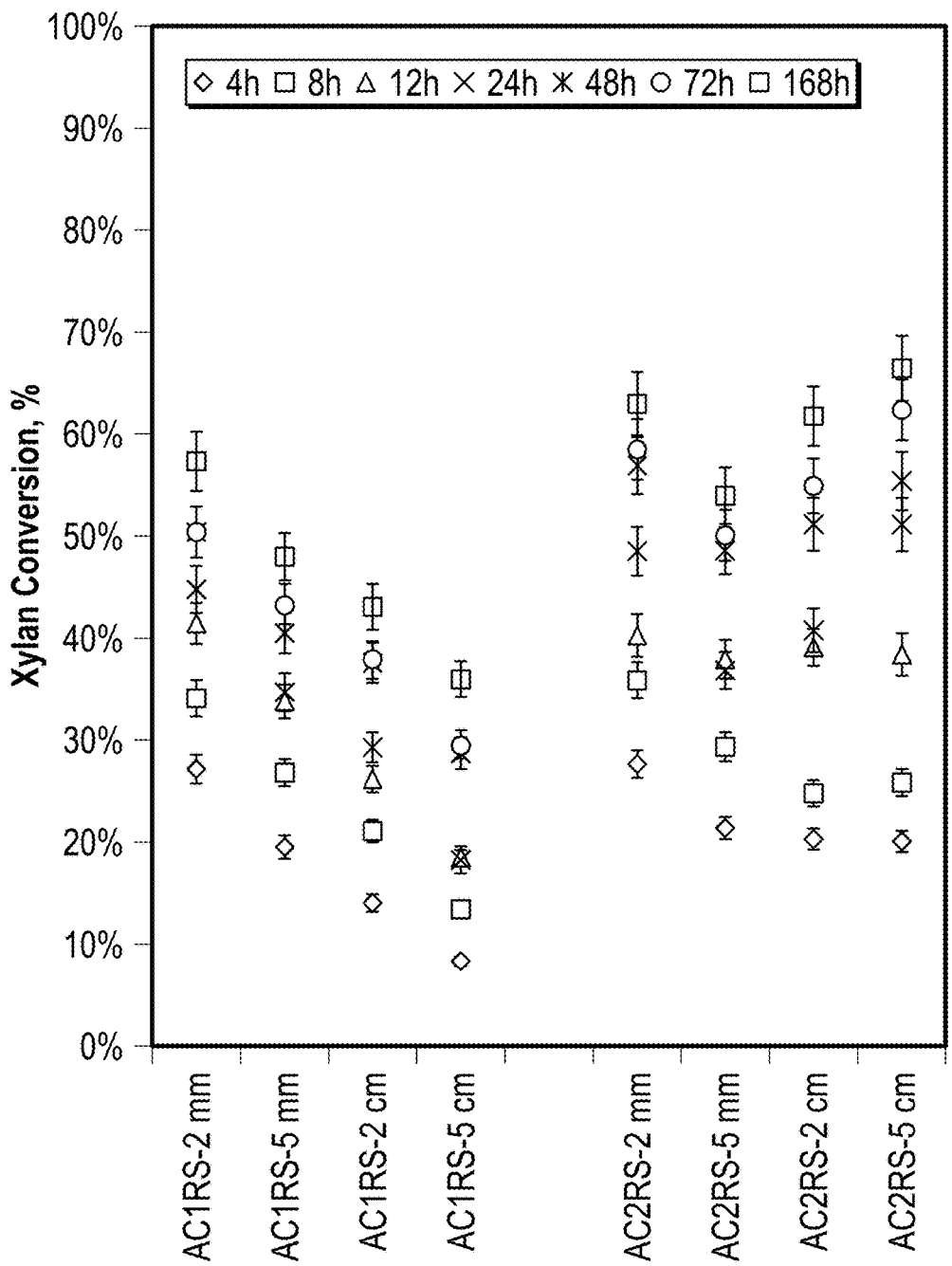

Hydrolysis of AC2RS substrates containing small versus large-sized particles demonstrated an opposite conversion trend. Specifically, AC2RS substrates containing smaller-sized particles (e.g., 2 mm and 5 mm) showed a decreasing sugar conversion trend as the size increased (i.e., AC2RS-2 mm>AC2RS-5 mm) which was similar to the smaller AC1RS substrates. Interestingly, for AC2RS substrates containing larger-sized particles (e.g., 2 cm and 5 cm) an increasing sugar conversion trend was noticed as the size increased (i.e., AC2RS-2 cm<AC2RS-5 cm). After 168 h hydrolysis, the largest particle size rice straw (AC2RS-5 cm) produced the highest glucan and xylan conversions, at 90.4% and 66.5%, respectively, when compared to the other particle size of AC2RS substrates pretreated under identical conditions (FIGS. 4A and 4B).

Figure 3C:
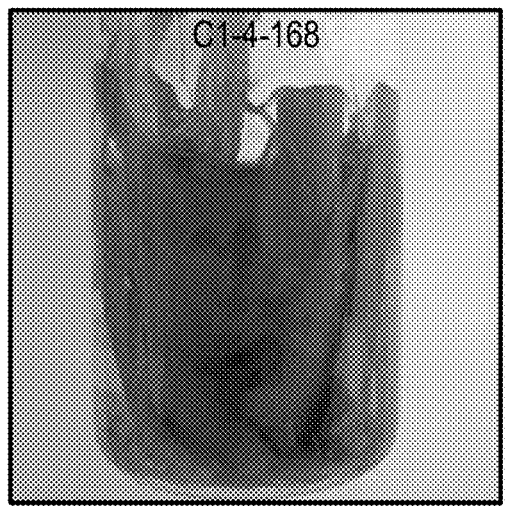
Figure 3D:
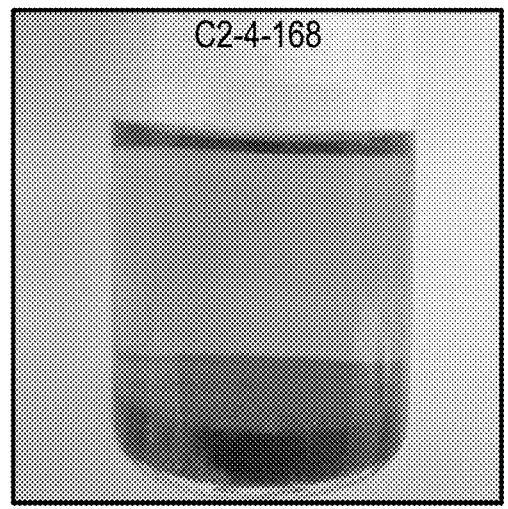
Figure 5A:
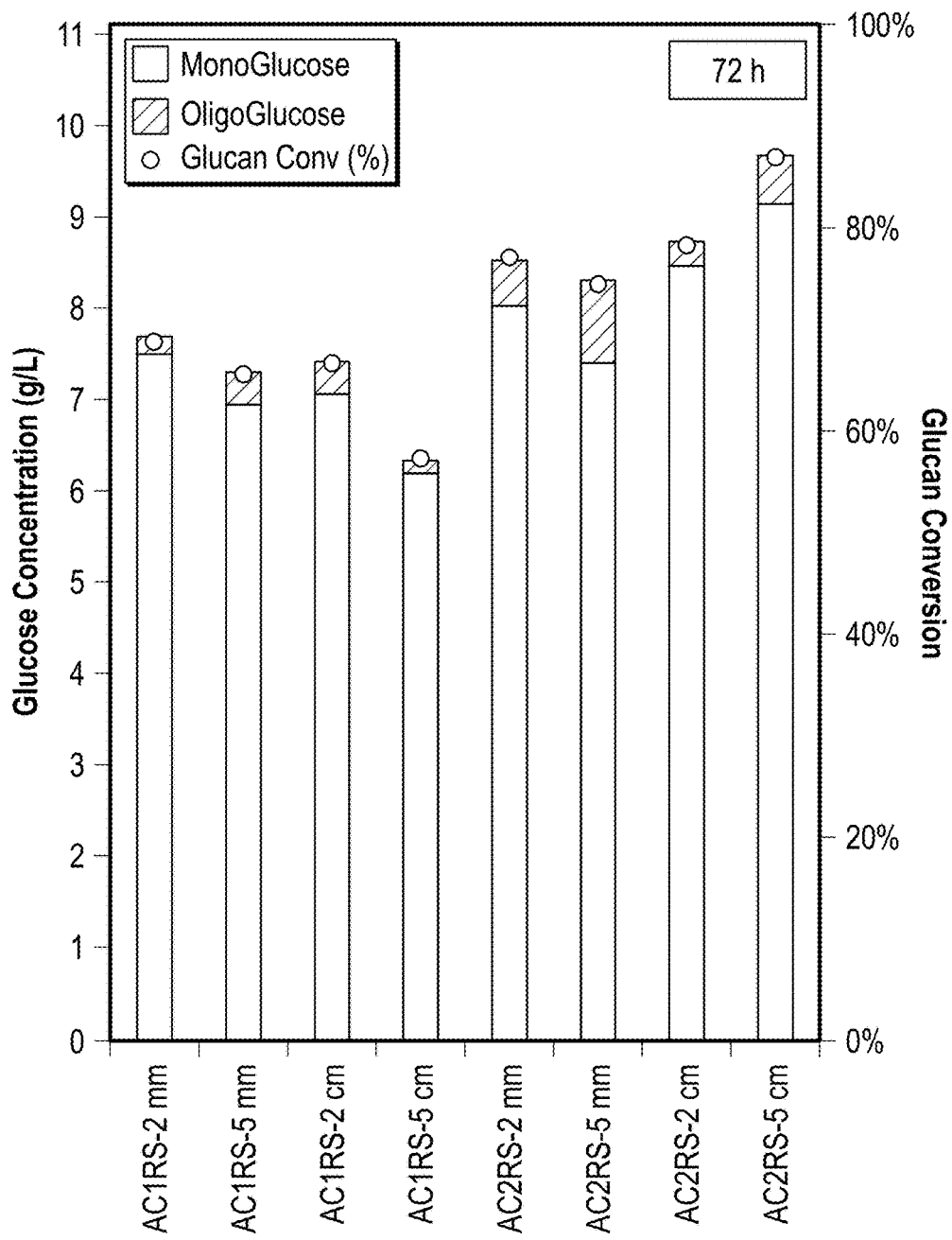
FIGS. 5A-5D are graphs showing comparisons of monomeric and oligomeric sugar concentrations and conversions at 1% GL for AC1RS and AC2RS at different hydrolysis periods and particle sizes, with FIGS. 5A and 5B showing glucose concentrations and glucan conversions, respectively, and FIGS. 5C and 5D showing xylose concentrations and xylan conversions, respectively, according to various embodiments.
Figure 5B:
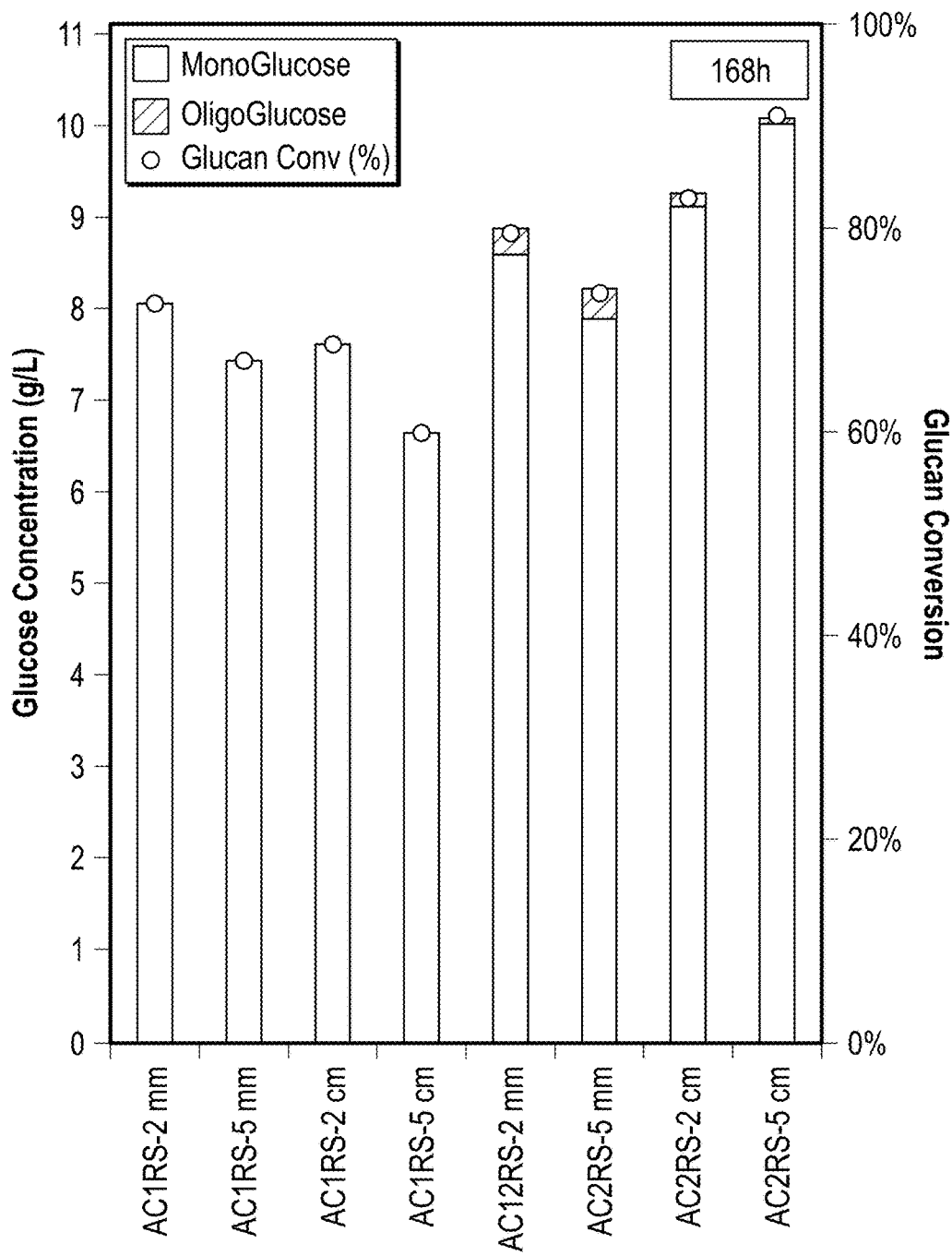
Figure 5C:
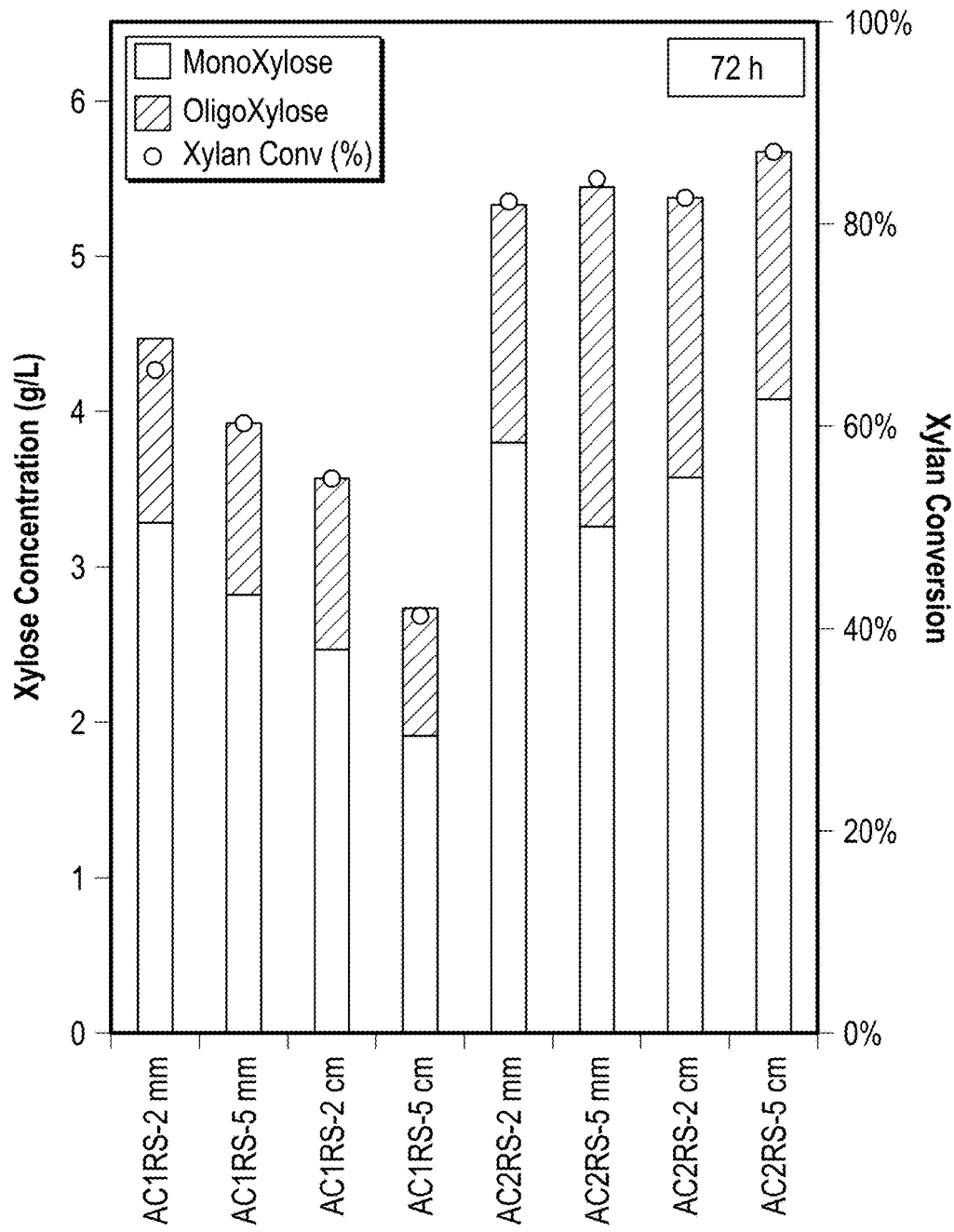
Figure 5D:
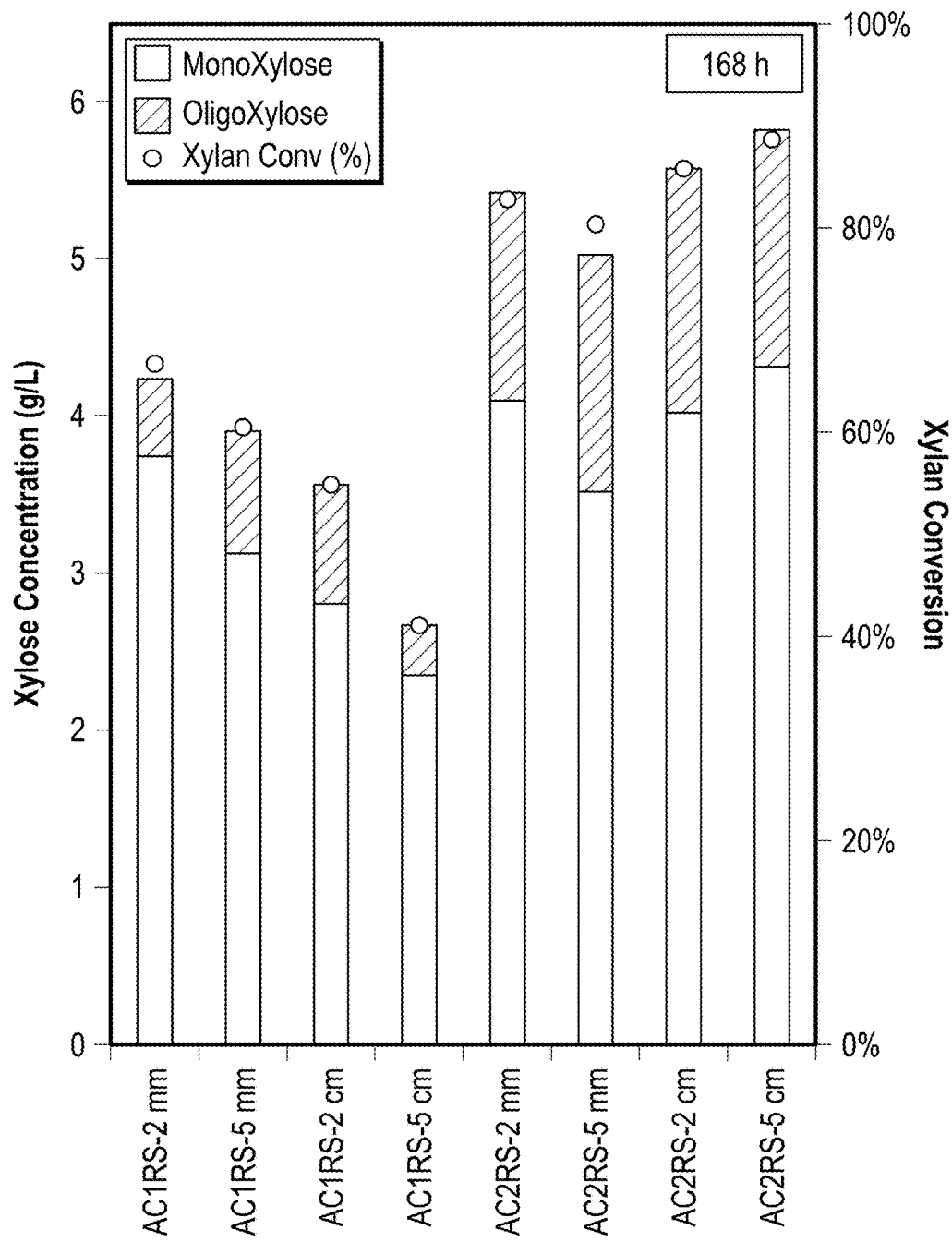

The largest particle rice straw (5 cm) (shown in FIGS. 3A and 3C) demonstrated qualitatively different digestion patterns during enzymatic hydrolysis when pretreated using different AFEX conditions. The substrate of AC1RS-5 cm hydrolyzed slowly and the particles remained intact with minor physical disintegration after 72 hrs of hydrolysis (FIG. 3A) and even after 168 h of hydrolysis (FIG. 3C), as evidenced by low sugar concentrations in the hydrolysate. The substrate of AC2RS-5 cm completely disintegrated after the same period of hydrolysis and only left fine particles in the hydrolysate (FIGS. 3A-3D), resulting in the highest sugar concentrations and therefore higher glucan and xylan conversions. In contrast, both sizes of milled rice straw (2 mm and 5 mm), when pretreated using AFEX™ C1 and AFEX™ C2 conditions, did not manifest any significant differences physically during hydrolysis nor in the sugar production.

substrates (both after 72 hr and 168 hr of hydrolysis) indicating the effectiveness of AFEX™ pretreatment conditions (C2 over C1). Increasing concentrations of monomeric sugars and decreasing amounts of oligomeric sugars were also evident as the hydrolysis proceeded (from 72 hr to 168 hr). Additionally, at the low GL, oligomeric xylose concentrations for AC1RS and AC2RS-treated substrates were much higher when compared to oligomeric glucose concentrations, averaging at least about a four-fold increase over oligomeric glucose concentrations (FIGS. 5A and 5C for 72 hr and FIGS. 5B and 5D for 168 hr of hydrolysis), with the majority of the xylose released in oligomeric form.

Most xylose was released in oligomeric form, with high concentrations of oligomeric xylose caused by insufficient xylanase activity in the commercial cellulase (Spezyme® CP mix) which led to a low concentration of monomeric xylose. Overall, after 72 hr (168 hr) hydrolysis, the highest glucose/xylose concentrations and glucan/xylan conversions (including the oligomeric sugar) were found to be 9.68/5.68 g/L (10.11/5.82 g/L) and 87.0%/87.2% (91.4%/88.7%) respectively for AC2RS-5 cm. This included oligomeric glucose/xylose concentrations of 0.54 g/L/1.61 g/L (0.07 g/L/1.5 g/L) and glucan/xylan 4.8%/24.6% (0.92%/22.2%) respectively. (See FIGS. 5A-5D).

Kinetic Modeling of AFEX™ Pretreated Rice Straw

A dominant factor affecting the enzymatic hydrolysis rate is the severity of the pretreatment conditions. The increased severity of the AC2RS conditions (log $R_o$=2.88) made the treated rice straw substrate, particularly the larger particles, more susceptible to enzymatic hydrolysis than AC1RS conditions (log $R_o$=1.48), and therefore increased the hydrolysis rate. The enzymatic hydrolysis data for URS, AC1RS and AC2RS substrates were fitted into the Chrastil diffusion-limited kinetic model based on Eq. (1) to further understand the kinetics of this unusual hydrolysis result. Table 3 sum-

TABLE 2

Sugar concentration at initial and final hydrolysis stage and sugar release rate (1% and 3% GL)

| | 1% GL | | | | | | 3% GL | | | | | |
|---|---|---|---|---|---|---|---|---|---|---|---|---|
| | Initial $C^a$ (g/L) | | Final $C^b$ (g/L) | | Release rate$^c$ (g/L · hr) | | Initial $C^a$ (g/L) | | Final $C^b$ (g/L) | | Release rate$^c$ (g/L · hr) | |
| Substrate | Glu | Xyl | Glu | Xyl | Glu | Xyl | Glu | Xyl | Glu | Xyl | Glu | Xyl |
| AC1RS - 2 mm | 4.2 | 1.8 | 8.1 | 3.7 | 0.51 | 0.22 | 10 | 4.2 | 22.4 | 9.9 | 1.24 | 0.52 |
| AC1RS - 5 mm | 3.7 | 1.3 | 7.5 | 3.1 | 0.46 | 0.18 | 9.5 | 3.3 | 21.8 | 8.7 | 1.23 | 0.42 |
| AC1RS - 2 cm | 2.8 | 0.9 | 7.6 | 2.8 | 0.41 | 0.14 | 7.2 | 2.7 | 22.0 | 8.2 | 1.1 | 0.38 |
| AC1RS - 5 cm | 1.6 | 0.5 | 6.7 | 2.4 | 0.31 | 0.1 | 5.8 | 2.2 | 19.9 | 7.0 | 0.94 | 0.32 |
| AC2RS - 2 mm | 4.5 | 1.8 | 8.6 | 4.1 | 0.51 | 0.22 | 6.1 | 2.6 | 22.1 | 10.2 | 0.90 | 0.38 |
| AC2RS - 5 mm | 4.1 | 1.4 | 7.9 | 3.5 | 0.51 | 0.21 | 5.1 | 2 | 20.3 | 8.6 | 1.06 | 0.36 |
| AC2RS - 2 cm | 4.1 | 1.3 | 9.2 | 4 | 0.57 | 0.21 | 7.7 | 3 | 27 | 10.6 | 1.16 | 0.42 |
| AC2RS - 5 cm | 4 | 1.3 | 10 | 4.3 | 0.59 | 0.21 | 7.4 | 3.2 | 29.4 | 11.5 | 1.16 | 0.48 |

$^a$After 4 hr of hydrolysis;
$^b$After 168 hr of hydrolysis;
$^c$Slope at 12 hr of hydrolysis Low Solid Loading Hydrolysis (1% GL)—Oligomeric Sugar Release FIGS. 5A-5D compare monomeric and oligomeric glucose/xylose levels after 72 hr and 168 hr hydrolysis for LCB particles of varying sizes under AC1RS and AC2RS pretreatment conditions. As shown, more oligomers of glucose and xylose (higher concentrations and conversions) were observed in AC2RS substrates when compared to AC1RS marizes the estimated kinetic parameters for URS, AC1RS and AC2RS substrates at 1% and 3%-GL hydrolysis. The parameters for each hydrolysis case were determined from experimental data using non-linear regression analysis. In all regression cases, a good agreement with the experimental results was obtained as indicated by coefficient of determination, $R^2$>0.95 (Table 3). Therefore, the diffusion characteristics of the substrate-enzyme system in each hydrolysis case could be determined from the parameters n and k.

TABLE 3

Estimated parameters for substrate-enzyme diffusion-limited kinetic model for URS and AFEX™ pretreated rice straw at different particle size and GL

| | 1% GL | | | | | 3% GL | | | | |
|---|---|---|---|---|---|---|---|---|---|---|
| | Diffusion-limited kinetic | | | Equilibrium sugar concentrations, $P_e$ at t = 168 h | | Diffusion-limited kinetic | | | Equilibrium sugar concentrations, $P_e$ at t = 168 h | |
| Substrate size | k (L/g · h) | n | $R^2$ (%) | Glucose (g/L) | Xylose (g/L) | k (L/g · h) | n | $R^2$ (%) | Glucose (g/L) | Xylose (g/L) |
| URS - 2 mm | 0.048 | 0.293 | 98.5 | 2.9 | 0.6 | — | — | — | — | — |
| URS - 5 cm | 0.031 | 0.285 | 99.0 | 2.7 | 0.5 | — | — | — | — | — |
| AC1RS - 2 mm | 0.100 | 0.296 | 99.3 | 8.1 | 3.7 | 0.0300 | 0.364 | 99.2 | 24.4 | 9.9 |
| AC1RS - 5 mm | 0.100 | 0.320 | 99.4 | 7.5 | 3.1 | 0.029 | 0.340 | 99.5 | 21.8 | 8.7 |
| AC1RS - 2 cm | 0.108 | 0.440 | 99.4 | 7.6 | 2.8 | 0.029 | 0.444 | 99.2 | 22 | 8.2 |
| AC1RS - 5 cm | 0.093 | 0.456 | 97.3 | 6.7 | 2.3 | 0.028 | 0.509 | 99.5 | 19.9 | 7.0 |
| AC2RS - 2 mm | 0.096 | 0.294 | 99.9 | 8.6 | 4.1 | 0.018 | 0.397 | 98.9 | 22.1 | 10.1 |
| AC2RS - 5 mm | 0.122 | 0.322 | 99.1 | 7.9 | 3.5 | 0.018 | 0.381 | 98.0 | 20.3 | 8.6 |
| AC2RS - 2 cm | 0.141 | 0.438 | 98.6 | 9.1 | 4.0 | 0.032 | 0.528 | 99.5 | 27.0 | 10.6 |
| AC2RS - 5 cm | 0.160 | 0.522 | 98.7 | 10.0 | 4.3 | 0.035 | 0.616 | 98.4 | 29.4 | 11.4 |

The changes in the values of the structural diffusion resistance coefficient, n, show the progress of the modification of the substrates. The n value for URS at 2 mm was higher than URS at 5 cm, indicating a smaller diffusion resistance for the former particle size, although the difference was not significant. Nonetheless, it is possible to use the n value and evaluate the extent of the structural modifications on the pretreated rice straw substrates for different AFEX™ pretreatment conditions and at different particle sizes. As shown, increasing the particle size from 2 mm to 5 cm in the enzymatic hydrolysis at 1% GL increased the n value for AFEX™ pretreated rice straw. The n value for AC1RS and AC2RS substrates ranged from 0.296 to 0.456 and from 0.294 to 0.522, respectively. Compared to URS, the change in n for AC1RS and AC2RS substrates yielded different scenarios for 2 mm and 5 mm particle sizes. While the n for the 2 mm substrate slightly changed from 0.293 in URS to 0.296 in AC1RS and 0.294 in AC2RS, the n for the 5 cm substrate increased from 0.285 in URS to 0.456 in AC1RS and 0.522 in AC2RS (Table 3).

This change of n value suggests that the relevant changes in the diffusion and the structure of the substrate-enzyme system have occurred after pretreatment, resulting in less diffusion resistance in the pretreated samples. Comparing the hydrolysis of AC1RS and AC2RS substrates, the smaller particle size (2 mm and 5 mm) for both substrate types produced almost similar n values ranging from 0.294 to 0.322 for 1% GL hydrolysis, and from 0.340 to 0.397 for 3% GL hydrolysis. A different n value was observed for larger particle sizes of AC1RS and AC2RS substrates (2 cm and 5 cm). The larger particle sizes of the AC2RS substrate expressed higher n values, 0.438 to 0.522, and 0.528 to 0.616 for 1% and 3% GL hydrolysis, respectively, compared to AC1RS substrates (Table 3). This result suggests that the AC2RS conditions using a larger particle size improved the diffusion of molecules in the pores of the substrate.

SEM Histological Changes of URS and AFEX™ Pretreated Rice Straw Epidermal

In addition to the quantitative analysis of the hydrolysis trends of AC1RS and AC2RS, the SEM analysis provided further understanding of the hydrolysis of the AC1RS and AC2RS substrates based on histological changes of the URS and AFEX™ pretreated rice straw epidermal surface.

SEM images of URS at small particle size (2 mm and 5 mm) show that most of the cuticle and silica layers on the surface were already broken during the milling process and this greatly aided the AC2RS condition as the surface resistance was less than un-milled straw. Although it was a mild pretreatment condition, most of the papillae, cuticle and silica layers, and possibly lignin and other extractives, were easily cooked, melted and solidified in situ by the AC1RS condition, thereby exposing the cellulose fibers, making them more accessible to enzymes and ready for the subsequent hydrolysis. These degraded and solidified materials on the epidermal surface yielded a messy and compact surface, as indicated by the low n value in the kinetic model.

When the small particle size substrate (2 mm and 5 mm) was severely pretreated with the AFEX™ C2 condition, the severity of this pretreatment not only cooked and melted the papillae, cuticle and silica layers, but it also degraded the exposed cellulose fibers, producing poor hydrolysis performance (image not shown). Although the surface of AC2RS-5 mm was quite clean and less compact compared to the surface of AC1RS-5 mm, indicating the impact of high severity in the AFEX™ C2 condition, the hydrolysis of this substrate, at low or high GL, normally yielded the lowest concentration and conversion due to cellulose degradation during pretreatment.

FIGS. 6A-6I shows the SEM images of the exterior epidermal surface of large particle size (2 cm and 5 cm) untreated rice straw (URS—6A-6C) and after AFEX™ pretreatment rice straw (AC1RS—6D-6F; AC2RS—6G-6I) samples. In AC1RS, some silica bodies were exposed on cellulose large fibrils due to removal of the cuticle layer by AC1RS pretreatment (FIG. 6E), as silica was deposited as a layer beneath the cuticle layer. While the cellulose configuration was still intact, some of the papillae structures were broken, showing the collapse of some cuticle layers, and the size of large lumps was also reduced. Most of the silicified short cells were still intact. Although the AC1RS condition could remove some cuticle layers, it was not adequate to make the cellulose more accessible to the enzymes. Poor hydrolysis was observed on AC1RS substrate with large particle size (2 cm and 5 cm).

On the other hand, SEM images show that AC2RS had a very clean and clear epidermal surface (FIG. 6G). Most of the papillae, cuticle and silica layers were diminished, and the large lumps together with lignin were deformed. These substances were condensed and agglomerated into large flakes (LF) which were redistributed on the particle surface resulting in a very clear view of the lump pits and twisted short cells. The cellulose fibers (CF) were clearly exposed to the surface with the dumbbell silica body (DSB) next to it indicating complete destruction and removal of the cuticle and silica layers. The absence of cuticle and silica layers, along with clean cellulose fibers, increased the cellulose accessibility to the enzymes, resulting in good digestibility and hydrolysis performance. This was also indicated by the high n and k values in the kinetic model of large particle of AC2RS substrates (2 cm and 5 cm). The interior epidermis of AC2RS also showed that the long cells were totally enlarged and started to disintegrate from the surface compared to URS and AC1RS substrates, resulting in higher digestibility (FIGS. 6A, 6D and 6I). High severity pretreatment conditions (AC2RS) in which the pretreatment temperature is 140° C., well above the glass transition temperature of lignin (120° C.), (should have helped ammonia to solubilize lignin and re-deposit it on the surface when ammonia is removed after pretreatment.

Comparison of Different GL Hydrolysis (1%, 3% and 6%)

Figure 7A:
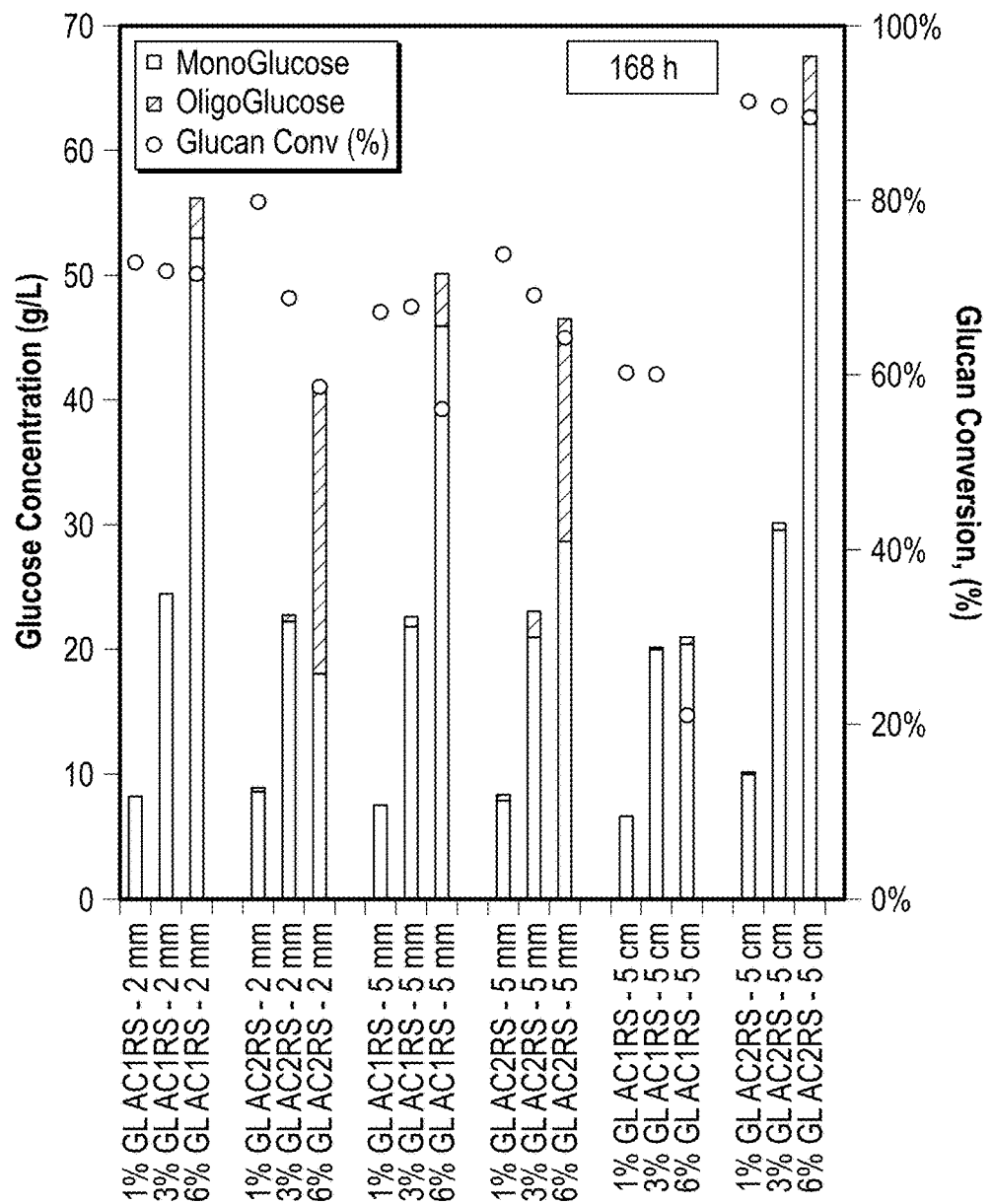
FIGS. 7A-7C are graphs showing comparisons of concentrations (FIG. 7A), conversions (FIG. 7B) and sugar yields (FIG. 7C) under hydrolysis at different GL for selected AC1RS and AC2RS particle sizes according to various embodiments.
Figure 7B:
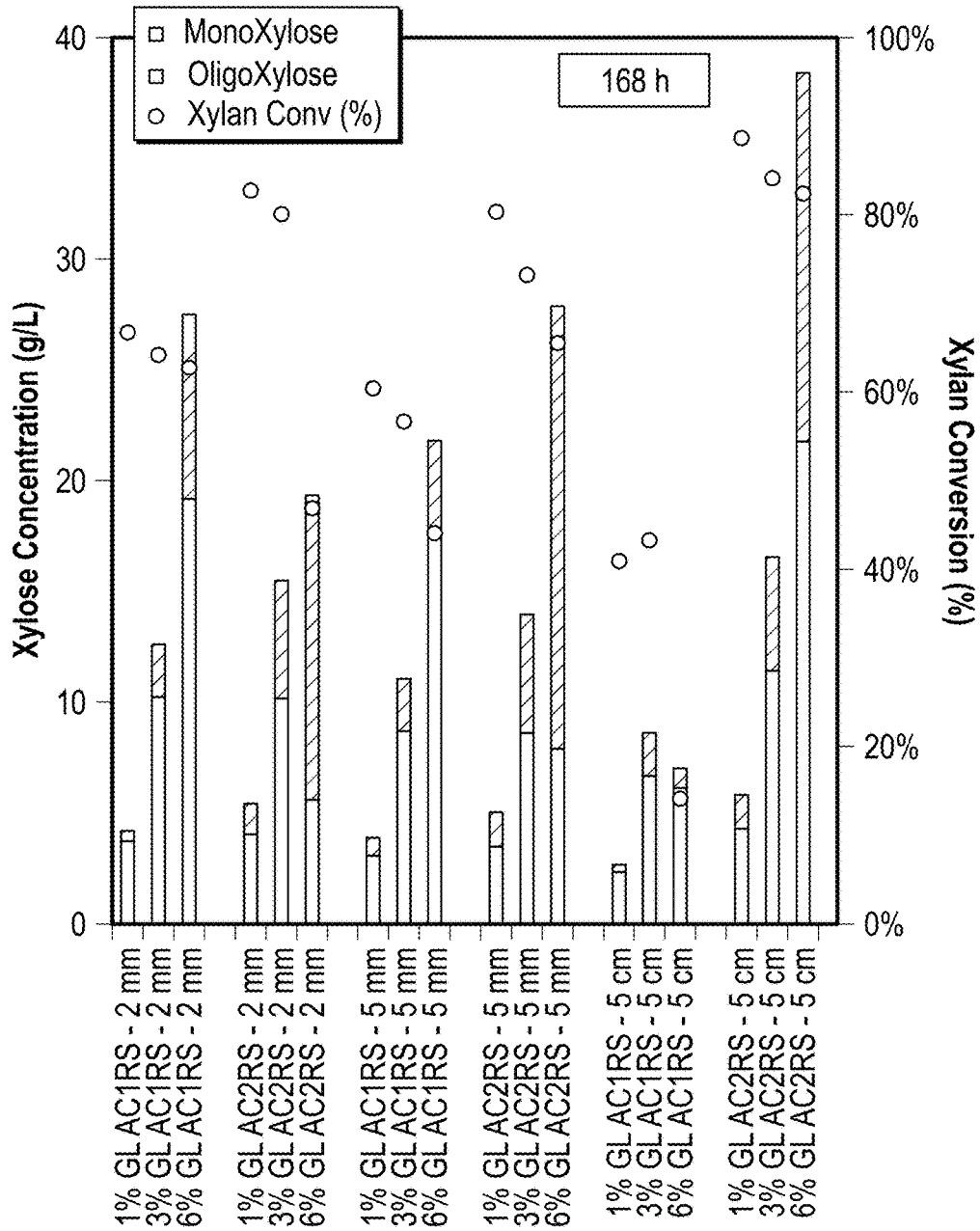

FIGS. 7A and 7B show a comparison of glucan and xylan conversions after 168 h of hydrolysis from low to high GL (1%, 3% and 6%) for AC and AC2RS substrates at 2 mm, 5 mm and 5 cm. As FIGS. 7A and 7B show, concentrations of monomeric and oligomeric glucose/xylose for most substrates increased (due to the increase in solid loading in the hydrolysis). Additionally, glucan and xylan conversions decreased as the GL increased from 1% to 6%. AC2RS-5 cm substrate continued to give the highest sugar concentrations (including the oligomeric sugars) and conversions at higher GL.

After 168 h hydrolysis, 3% GL AC2RS, the glucose/xylose conversion 5 cm substrates were 90.7%/84.1%, respectively; and, at 6% GL the glucan/xylan conversions were 89.4%/82.5, respectively.

It appears that the combined effect of the and mass transfer limitation and pretreatment severity affected the performance of the smaller-sized AC1RS and AC2RS substrates in the hydrolysis at higher GL (3% and 6%). At high GL, particularly at 3% GL, small-sized AC1RS and AC2RS substrates in their granular forms agglomerated easily when water was added, resulting in thick slurries of hydrolysis mixture which were difficult to uniformly mix (FIG. 5A-D). At initial stages, hydrolysis of smaller-sized AC1RS substrates at 3% GL produced higher initial glucose/xylose concentrations and higher glucose/xylose release rate when compared to the smaller-sized AC2RS substrates (Table 3).

The (low severity) AC1RS conditions (in combination with the shorter residence time) provided milder treatment to AC1RS substrates, resulting in less LCC cleavage, less hemicellulose release and less lignin redistribution. It is possible that these conditions also reduced the hydrodynamic interactions between the larger particles and surrounding fluid, as well as interaction among the particles, thus interfering less with enzyme diffusion as compared to smaller-sized particles. Although smaller-sized AC1RS substrates had poor surface condition due to in situ degradation and solidification of papilla, cuticle and silica layers, and possibly lignin and other extractives, the cellulose fibers were successfully cleaned and perfectly exposed for better enzyme accessibility which produced better sugar hydrolysis than milled AC2RS. (FIGS. 7A and 7B)

Similar n values for smaller particle size of AC1RS and AC2RS substrates (2-5 mm) indicated that the diffusion resistance was approximately the same in both substrates. The k values in AC1RS-2 mm (0.030 L/g·h) and AC1RS-5 mm (0.029 L/g·h) substrates were much higher compared to AC2RS of the same size (0.0184 L/g·h for AC2RS-2 mm and 0.018 L/g·h for AC2RS-5 mm) possibly due to cellulose fiber degradation in the latter substrates resulting in less cellulose hydrolysis (Table 3).

As observed during hydrolysis at 1% GL, hydrolysis of AC1RS and AC2RS substrates at high GL (3% and 6%) generally released higher concentrations of oligomeric xylose than oligomeric glucose, as shown in FIGS. 7A and 7B. The combination of Spezyme® CP and Novozyme® 188, used in the hydrolysis, could not efficiently hydrolyze the oligomeric xylose to monomeric xylose due to insufficient β-xylosidase activity in the enzyme preparations. Coupled with fast hydrolysis of xylan to oligomeric xylose, this led to the high concentration of oligomeric xylose and low concentrations of monomeric xylose, particularly in small particle size AC2RS substrates. This condition probably inhibited the cellulase activity and reduced the cellulose hydrolysis which led to high concentrations of oligomeric glucose in small particle size AC2RS substrates.

However, hydrolysis of larger-sized (cm range) AC1RS and AC2RS-substrates at 3% GL showed a different trend as compared to smaller-sized (mm range) AC1RS and AC2RS substrates at the same GL. Both AC2RS-2 cm and AC2RS-5 cm substrates produced the highest glucose/xylose concentrations among all substrates at 3% GL hydrolysis (Table 3). At low (1%) and high (3% and 6%) GL hydrolysis, AC2RS-5 cm substrate behaved very differently than AC1RS-5 cm substrate. The former gave the highest glucose and xylose concentrations after 72/168 h of hydrolysis even at high solid loading (3% and 6% GL) while the latter yielded the lowest sugar concentrations at all GLs (FIGS. 7A and 7B). The substrate of AC2RS-5 cm completely disintegrated and solubilized into water and left only fine and "powdery-looking" particles, even when the solid loading of the hydrolysis was increased as previously shown (FIGS. 3A-3D). The Chrastil kinetic model indicates that for hydrolysis at 3% GL, AC2RS-5 cm had the highest n and k values (0.616 and 0.0345 L/g·h) followed by AC2RS-2 cm substrates (0.528 and 0.0323 L/g·h) while AC1RS-5 cm gave low k value (0.0282 L/g·h) at a reasonably high n value (0.509). These kinetic parameters showed that the large particle size substrates, when severely pretreated with the AFEX™ C2 condition, actually had less diffusion resistance with increased catalytic hydrolysis properties, compared to the smaller particle size. This interpretation of hydrolysis kinetics was visually confirmed with SEM imaging analysis of AC2RS.

FIGS. 7A and 7B compare the glucan and xylan conversion after 168 hr of hydrolysis at GL of 1%, 3% and 6% for AC1RS and AC2RS substrates having a particle size of about 2 mm, 5 mm and 5 cm. Theoretically, when the solid loading in the hydrolysis is increased, sugar concentrations should increase. From FIGS. 7A and 7B, it is clear that the concentrations of monomeric and oligomeric glucose/xylose for most substrates increased while glucan conversions decreased as the solid loading increased from 1% to 6% GL. The AC2RS-5 cm substrates continued to give the highest sugar concentrations (including the oligomeric sugars) and conversions at higher GL. After 168 hr hydrolysis, the glucose/xylose concentrations and glucan/xylan conversions were found to be 30.2 g/L/16.52 g/L and 90.7%/84.1% respectively at 3% GL and 67.47 g/L/38.38 g/L and 89.4%/82.5 respectively at 6% GL.

However, hydrolysis of AC2RS-2 mm and AC2RS-5 mm substrates at 6% GL showed less favorable results. At the end of 168 hr, the hydrolysis of both sizes of the smaller-sized AC2RS substrates at 6% GL produced extremely low concentrations of monomeric sugars, even lower than the concentrations at 3% GL, and some amount of cellobiose remained in the hydrolysate (shown in oligomeric glucose concentration).

Poor hydrolysis of small-sized AC2RS substrates at high GL (3% and 6%) were affected by the combined effect of pretreatment severity and diffusion limitation (low n and k values) as previously explained. As the hydrolysis progressed, the substrates were quickly hydrolyzed and fragmented into smaller sugar polymers and finally into cellobiose.

Figure 7C:
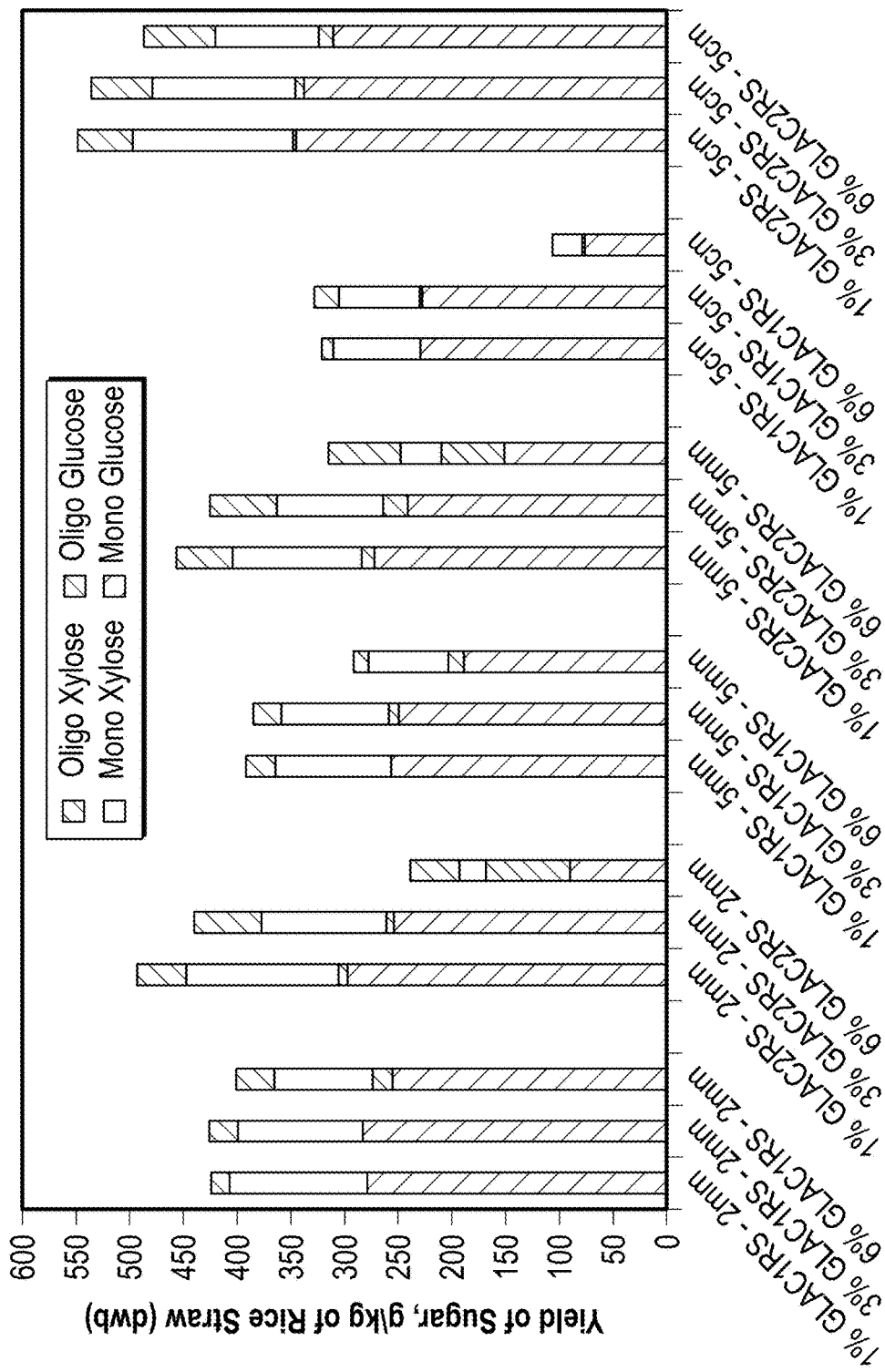

FIG. 7C shows the sugar yield for hydrolysis at different GLs per dry weight of AC1RS and AC2RS (2 mm, 5 mm and 5 cm). The yield of monomeric glucose and xylose decreased while the yield of oligomeric glucose and xylose increased when the GL increased from 1% to 6%. Among the substrates, AC2RS-5 cm demonstrated a consistent decreasing sugar yield as the GL increased. Hydrolysis at 6% GL revealed that the highest sugar yield was given by AC2RS-5 cm with a yield of 486.12 g/kg of rice straw (76% of the total theoretical maximum sugar yield with an average conversion of 85.9% from total glucan and xylan). On the other hand, AC1RS-5 cm gave the lowest sugar yield with only 107.6 g/kg of rice straw, about 16.8% of the total theoretical maximum sugar yield, and equivalent to one-quarter of the AC2RS-5 cm sugar yield. As for AC1RS substrates, hydrolysis at 6% GL indicated that AC1RS-2 mm also could produce reasonable sugar yields with 400.6 g/kg of rice straw (62% of the total theoretical maximum sugar yield).

Two optimized AFEX™ pretreatment conditions of different severities were successfully used to pretreat different particle sizes of rice straw, from conventionally-sized LCB particles of 5 mm or less, as well as larger-sized LCB particles having at least one dimension greater than 5 mm, up to about 5 cm. Regardless of the method of processing the rice straw, for a given size, AC2RS substrates achieved higher downstream sugar yields as compared to AC1RS substrates, thus demonstrating the greater effectiveness of AC2RS conditions.

While AC1RS substrates showed declining sugar yields as the size of-the substrates increased, surprisingly, AC2RS substrates demonstrated increasing sugar yields between smaller and larger-sized substrates. As with smaller-sized AC1RS substrates, the smaller-sized (conventional) AC2RS substrates also showed decreasing sugar yields as the particle size increased.

Surprisingly, larger particle size AC2RS substrates exhibited an increasing sugar yield when the substrate size increased. When treated using different AFEX™ conditions, the larger rice straw particles (5 cm) demonstrated different digestion patterns during enzymatic hydrolysis. While the AC1RS-5 cm substrate hydrolyzed slowly and solids remained intact with minor physical disintegration, the AC2RS-5 cm substrate completely disintegrated after the same period of hydrolysis and only left fine particles in the hydrolysate. The Chrastil diffusion-limited kinetic model was able to model the experimental data and explain the hydrolysis behavior at different particle size based on kinetic parameters, k and n. Analysis of SEM imaging supported our interpretation of the experimental hydrolysis behavior and kinetic data.

Example 2 (Prophetic)

Additional testing with larger-sized particles, such as up to about 10 cm or higher, including, for example, particles having at least one dimension no less than about 6 cm, 7 cm, 8 cm, 9 cm, 10 cm, and higher, may also be performed.

Additional testing with other types of AFEX™ pretreatment methods may also be performed, including, for example, gaseous ammonia pretreatment (GAP) and/or anhydrous liquid ammonia pretreatment and/or (E-AFEX™). See, for example, PCT Applications 20111133571, US2011/066868, and US2010/035826, each of which is incorporated herein in its entirety.

Additional testing with higher GLs and/or different ammonia to biomass ratios and/or different moisture content and/or different residence times and/or different temperatures may also be performed.

Additional testing with other types of LCB may also be performed, such as, for example, corn stover and switchgrass.

Various combinations of the above parameters may also be tested.

Therefore, in various embodiments a method of increasing sugar yield in a bio-product production process is provided comprising pretreating one or more size-adjusted lignocellulosic biomass particles with a pretreatment, wherein the one or more size-adjusted lignocellulosic biomass particles (LCB) form a substrate, with the one or more particles having an average particle size in at least one dimension greater than 5 mm. In one embodiment, the pretreatment process is an ammonia pretreatment (AFEX™) process (e.g., gaseous ammonia, aqueous ammonia, anhydrous liquid ammonia, extractive ammonia, etc.) and one or more particles have an average particle size between about 1 cm and about 10 cm in at least one dimension and glucan loading is between about 1% and about 6% or about 1% and about 9%.

In one embodiment, the ammonia pretreatment process is a high severity ammonia pretreatment process, such as a process that operates at a temperature of no less than 140° C. and a residence time of no less than 30 minutes.

In one embodiment, a high severity ammonia pretreatment process is used. In such an embodiment, an ammonia to lignocellulosic biomass ratio can be, for example, between about 0.5:1 and about 4:1 and a moisture content of the lignocellulosic biomass can be, for example, between about 10% and 130%, on a dry weight basis. In one embodiment, a high severity ammonia pretreatment process is used and an ammonia to lignocellulosic biomass ratio can be no more than 1:1 and a moisture content of the lignocellulosic biomass can be no less than 130%, on a dry weight basis.

In one embodiment, the ammonia:LCB ratio is no more than about 1:1 and a moisture content of the LCB is no less than about 130%, on a dry weight basis. In one embodiment, the ammonia:LCB ratio is between about 0.5:1 and about 2:1 and a moisture content of the LCB is between about 10% and 130%, on a dry weight basis.

In one embodiment, the average particle size in a substrate is between about 4.5 and about 5.5 cm in at least one dimension and the substrate can be subjected to a high severity ammonia pretreatment, wherein a downstream xylose concentration is more than two times higher than a xylose concentration of a similarly-sized substrate subjected to a low severity ammonia pretreatment. In one embodiment, downstream sugar yield is increased by at least 1% up to about 150% or higher as compared with the low severity pretreatment.

It is possible that other pretreatment processes may work, including, but not limited to, dilute acid, concentrated acid, hydro-thermolysis, liquid hot water, acid catalyzed steam explosion, wet oxidation and heat.

The LCB particles can include, but are not limited to a perennial grass, an annual grass (e.g., rice straw) and agricultural residue (e.g., switch grass, corn stover, and the like). Such particles can be hydrolyzed with one or more enzymes, such as a cellulase enzyme or a beta-glucosidase enzyme.

A method of using a substrate to increase downstream sugar yield is also provided, such method comprising pretreating the substrate containing size-adjusted lignocellulosic biomass particles (LCB) with a pretreatment (e.g., ammonia pretreatment) to increase the downstream sugar yield, wherein the LCB particles have an average particle size in at least one dimension greater than 5 mm.

In various embodiments, a system is also provided, comprising, for example, a size-adjusting device for producing size-adjusted non-fine biomass; and a pretreatment facility for pretreating the size adjusted biomass to produce pretreated size-adjusted biomass, wherein the pretreated size-adjusted biomass increases sugar yield in a bio-product production facility as compared to fine biomass. Such a system can further comprise the bio-product production facility. The bioproduct can be, for example, a biofuel (ethanol, butanol) or animal feed. The size-adjusted non-fine biomass can have, in one embodiment, an average particle size greater than 5 mm in at least one dimension. In one embodiment, the size-adjusted non-fine biomass has an average particle size between about 1 cm and 10 cm.

Until now, it had been generally understood that fine grinding and/or milling of harvested LCB to average particle sizes below 5 mm resulted in a better yield under certain conditions by creating additional surface area which allowed the enzymes used for hydrolysis to more efficiently contact the LCB. In contrast, and surprisingly, even with use of larger particles, downstream sugar yield is improved. This is likely due to the presence of additional extractive material which has been solubilized by ammonia and re-deposited on the surface of the LCB particles after pretreatment (see FIGS. 6A-6I). In fact, rather than having less surface area, it appears that the additional extractive material produced with the non-fine LCB particles causes the LCB particles to become more porous, which actually increases the amount of surface area available on which the enzyme can act. This may be the reason that, in one embodiment, a higher digestibility, i.e., a higher sugar conversion, is observed with a high severity pretreatment, rather than a low severity pretreatment.

Additionally, use of conventionally-sized LCB particles which are less than 5 mm in size and/or with a particle size distribution of from about 0.2 mm to about 5 mm, including any value or range therebetween, form a solution containing fine particulates after pretreatment. Such a solution has an appearance comparable to that of "mud" or a "thick muddy solution." In contrast, use of LCB particles greater than 5 mm in size (in at least one dimension) up to about 5 cm in size or higher (in at least one dimension) in the embodiments described herein, including any size distribution therebetween, can form, in one embodiment, a particulate-containing solution having a viscosity comparable to that of either water or a "thin muddy solution."

While not wishing to be bound by this proposed theory, it is possible that the fine particulate-containing solution resulting from use of conventionally sized particles (e.g., less than 5 mm in size in any dimension), reduces mass transfer rates and thus enzyme hydrolysis while the larger particles described herein produce a solution which results in greater mass transfer rates and hence improved enzyme hydrolysis, as compared with the conventional method.

The various embodiments described herein have a further benefit of providing cost reduction, since less energy is expended in the size-adjusting step as compared to conventional methods. Specifically, rather than requiring fine grinding, crushing and/or fine milling of LCB particles, which can be quite difficult for some portions of the LCB, such as the stems, the mechanical processing step used herein is more economical. As such, the size-adjusting step in the embodiments described herein can involve milling, cutting, and/or chopping of the LCB particles into non-fine particle sizes (i.e., average particle size greater than 5 mm) With this process, the starting materials used herein for production of a bio-product from LCB are produced at less cost than the starting materials produced using conventional methods. If desired, one can perform the pretreatment process using the non-fine LCB particles as described herein, and then size reduce the pretreated LCB particles to any desired smaller size after pretreatment, prior to hydrolysis and/or fermentation.

Although specific embodiments have been illustrated and described herein, it will be appreciated by those of ordinary skill in the art that any procedure that is calculated to achieve the same purpose may be substituted for the specific embodiments shown. For example, although the process has been discussed using rice straw, other types of LCB can likely also be used, such as "empty fruit bunch" i.e., a material obtained from oil palm/date palm trees after removing the fruits the fibrous bunch. Furthermore, although the pretreatment has been discussed primarily as an ammonia pretreatment, it is possible that other pretreatments, as defined herein, can work as well. This application is intended to cover any adaptations or variations of the present subject matter. Therefore, it is manifestly intended that embodiments of this invention be limited only by the claims and the equivalents thereof.

What is claimed is:

1. A method comprising pretreating size-adjusted lignocellulosic biomass (LCB) particles with a pretreatment process to produce pretreated size-adjusted LCB particles which form a substrate, wherein said size-adjusted LCB particles have an average particle size in at least one dimension from about 1 cm to about 10 cm, wherein said pretreated size-adjusted LCB particles produce a higher sugar yield in a downstream bio-product production process as compared to pretreated LCB particles having a smaller or larger average particle size, wherein a glucan loading during hydrolysis in the downstream bio-product production process is from about 1% to about 9%, wherein the pretreatment process is a high severity ammonia fiber expansion (AFEX) pretreatment process selected from gaseous ammonia, aqueous ammonia, anhydrous liquid ammonia, and extractive ammonia, and wherein the downstream bio-product production process produces a bio-product.

2. The method of claim 1 wherein the high severity ammonia pretreatment process operates at a temperature of no less than 140° C. and a residence time of no less than 30 minutes.

3. The method of claim 1 wherein an ammonia to lignocellulosic biomass ratio is from about 0.5:1 to about 4:1 and a moisture content of the size-adjusted lignocellulosic biomass prior to pretreatment is from about 10% to 130%, on a dry weight basis.

4. The method of claim 1 wherein an ammonia to lignocellulosic biomass ratio is no more than 1:1 and a moisture content of the lignocellulosic biomass is no less than 130%, on a dry weight basis.

5. The method of claim 1 wherein the average particle size is from about 4.5 to about 5.5 cm in at least one dimension and the substrate is subjected to a high severity ammonia pretreatment, wherein a downstream xylose concentration is more than two times higher than a xylose concentration of a similarly-sized substrate subjected to a low severity ammonia pretreatment.

6. The method of claim 5 wherein the downstream sugar yield is increased by at least 1% up to about 150% or higher as compared to a similarly-sized substrate subjected to a low severity ammonia pretreatment.

7. The method of claim 1 wherein the LCB particles are selected from a perennial grass, an annual grass, agricultural residue, and combinations thereof.

8. The method of claim 7 wherein the annual grass is rice straw and the agriculture residue is switchgrass or corn stover.

9. The method of claim 1 wherein the bio-product is a biofuel or animal feed.

10. The method of claim 9 wherein the biofuel is ethanol or butanol.

11. The method of claim 1 wherein said LCB particles are hydrolyzed with one or more enzymes.

12. The method of claim 11 wherein the one or more enzymes comprise one or more cellulase enzymes.

13. The method of claim 1 wherein the glucan loading is from about 1% to about 6%.

14. A method comprising pretreating one or more size-adjusted lignocellulosic biomass (LCB) particles with a pretreatment to produce pretreated size-adjusted LCB particles which form a substrate, wherein said size-adjusted LCB particles have an average particle size in at least one dimension greater than 0.5 cm, wherein said pretreated size-adjusted LCB particles produce a higher sugar yield in a downstream bio-product production process, as compared to pretreated LCB particles having an average particle size in at least one dimension less than 0.5 cm, and wherein the pretreatment process is a high severity ammonia fiber expansion (AFEX) pretreatment process selected from gaseous ammonia, aqueous ammonia, anhydrous liquid ammonia, and extractive ammonia.

15. The method of claim 14 wherein the bio-production process includes a hydrolysis step and the method further comprises subjecting said pretreated size-adjusted LCB particles to the hydrolysis step to produce the increased sugar yield.

16. The method of claim 14 further comprising size-adjusting said LCB particles.

17. The method of claim 15 wherein glucan loading during the hydrolysis is from about 1% to about 9%.

* * * * *

UNITED STATES PATENT AND TRADEMARK OFFICE
CERTIFICATE OF CORRECTION

PATENT NO. : 10,202,660 B2  
APPLICATION NO. : 14/382370  
DATED : February 12, 2019  
INVENTOR(S) : Venkatesh Balan et al.

Page 1 of 2

It is certified that error appears in the above-identified patent and that said Letters Patent is hereby corrected as shown below:

On the Title Page

Item (56), Other Publications/Page 4/Column 2/Tolan/Line 39: Error reads as "– logen's" and should read as "Iogen's"
Item (56), Other Publications/Page 5/Column 1/Zhou/Line 43: Error reads as "P2 ?" and should read as "P2"
Item (56), Other Publications/Page 6/Column 2/Adapa/Line 18: Error reads as "Internation Journal" and should read as "International Journal"
Item (56), Other Publications/Page 6/Column 2/Chahal/Line 67: Error reads as "Production form" and should read as "Production from"
Item (56), Other Publications/Page 7/Column 1/Renewals Fuel Association/Lines 50-51: Error reads as "<http://http://www.ethanolrfa.org/refinery-locations/," and should read as "<https://ethanolrfa.org/resources/biorefinery-locations/>"

In the Specification

Column 4/Line 6: Error reads as "chain alkanes" and should reads as "chain alkanes,"
Column 4/Line 29: Error reads as "limited wet" and should read as "limited to wet"
Column 5/Lines 41-42: Error reads as "Pectate may be "decorated" with mannose or rahmnose sugars, also)." and should read as "Pectate may also be "decorated" with mannose or rahmnose sugars."
Column 8/Line 16: Error reads as "low severity pretreatment conditions," and should read as "low severity pretreatment conditions are provided,"
Column 13/Line 14: Error reads as "using high" and should read as "using a high"
Column 13/Line 38: Error reads as "particle size)" and should read as "particle size"
Column 23/Line 20: Error reads as "(should" and should read as "should"
Column 23/Line 38: Error reads as "89.4%/82.5," and should read as "89.4%/82.5%,"
Column 23/Line 39: Error reads as "of the and mass" and should read as "of the mass"
Column 24/Lines 66-67: Error reads as "89.4%/82.5" and should read as "89.4%/82.5%,"

Signed and Sealed this  
Seventh Day of May, 2019

Andrei Iancu  
*Director of the United States Patent and Trademark Office*

CERTIFICATE OF CORRECTION (continued)
U.S. Pat. No. 10,202,660 B2

Column 26/Lines 11-13: Error reads as "See, for example, PCT Applications 20111133571,US2011/066868, and US2010/035826, each of which is incorporated herein in its entirety." and should read as "See, for example, PCT Applications WO20111133571, PCT/US2011/066868, and PCT/US2010/035826, each of which is incorporated herein in its entirety."